(12) United States Patent
Watkins et al.

(10) Patent No.: US 8,143,394 B2
(45) Date of Patent: Mar. 27, 2012

(54) PYRIDO(3,2-D)PYRIMIDINES USEFUL FOR TREATING VIRAL INFECTIONS

(75) Inventors: William John Watkins, Saratoga, CA (US); Lee Shun Chong, Newark, CA (US); Jennifer R. Zhang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 40 days.

(21) Appl. No.: 12/519,496

(22) PCT Filed: Dec. 24, 2007

(86) PCT No.: PCT/EP2007/011494
§ 371 (c)(1),
(2), (4) Date: Jun. 16, 2009

(87) PCT Pub. No.: WO2008/077649
PCT Pub. Date: Jul. 3, 2008

(65) Prior Publication Data
US 2009/0324543 A1 Dec. 31, 2009

Related U.S. Application Data

(60) Provisional application No. 60/871,905, filed on Dec. 26, 2006.

(51) Int. Cl.
*C07D 471/00* (2006.01)
*C07D 487/00* (2006.01)
(52) U.S. Cl. ..................................... 544/279
(58) Field of Classification Search ............... 514/264.1, 514/264.11; 544/279
See application file for complete search history.

(56) References Cited

U.S. PATENT DOCUMENTS

| | | | |
|---|---|---|---|
| 2,924,599 A | 2/1960 | Oakes et al. | |
| 3,939,268 A | 2/1976 | Nickl et al. | |
| 4,460,591 A | 7/1984 | DeGraw et al. | |
| 5,167,963 A | 12/1992 | DeGraw et al. | |
| 5,508,281 A | 4/1996 | Gangjee | |
| 5,521,190 A | 5/1996 | Henrie, II et al. | |
| 5,654,307 A | 8/1997 | Bridges et al. | |
| 6,476,031 B1 | 11/2002 | Chakravarty et al. | |
| 6,713,484 B2 | 3/2004 | Bridges et al. | |
| 6,723,726 B1 | 4/2004 | Cockerill et al. | |
| 6,730,682 B2 | 5/2004 | Schnute et al. | |
| 2002/0049207 A1 | 4/2002 | McCarthy | |
| 2003/0186987 A1 | 10/2003 | Bridges et al. | |
| 2003/0199526 A1 | 10/2003 | Choquette et al. | |
| 2004/0039000 A1 | 2/2004 | Gangjee | |
| 2004/0106616 A1 | 6/2004 | Bakthavatchalam et al. | |
| 2008/0182870 A1* | 7/2008 | Bondy et al. | 514/303 |
| 2009/0131414 A1* | 5/2009 | De Jonghe et al. | 514/218 |
| 2010/0048559 A1* | 2/2010 | Bondy et al. | 514/234.2 |

FOREIGN PATENT DOCUMENTS

| | | |
|---|---|---|
| WO | WO-01/83456 A1 | 11/2001 |
| WO | WO-02/22602 A2 | 3/2002 |
| WO | WO-02/22607 A1 | 3/2002 |
| WO | WO-03/062209 A2 | 7/2003 |
| WO | WO 2006/069805 * | 7/2006 |
| WO | WO-2006/069805 A2 | 7/2006 |
| WO | WO 2006/135993 * | 12/2006 |
| WO | WO-2006/135993 A1 | 12/2006 |

OTHER PUBLICATIONS

Baba et al. (1984) "Synergistic Antiviral Effects of Antiherpes Compounds and Human Leukocyte Interferon on Varicella-Zoster Virus In Vitro," *Antimicrobial Agents and Chemotherapy* 25(4):515-517.
Elion et al. (1954) "Antagonists of Nucleic Acid Derivatives," *J. Biol Chem.* 208:477-488.
International Search Report and Written Opinion for PCT/EP2007/011494, International Filing Date Dec. 24, 2007.

* cited by examiner

*Primary Examiner* — Andrew D Kosar
*Assistant Examiner* — Erich A Leeser

(57) ABSTRACT

2-amino-pyrido(3,2-d)pyrimidine derivatives with a specific substitution pattern on positions 4 and 6 of the core structure are useful in the treatment or prevention of an infection due to a virus from the Flaviviridae family, especially HCV, when administered to a patient in a therapeutically effective amount.

2 Claims, 2 Drawing Sheets

PYRIDO(3,2-D)PYRIMIDINES USEFUL FOR TREATING VIRAL INFECTIONS

This is a U.S. national stage application of PCT/EP2007/011494, filed, Dec. 24, 2007, filed under 35 U.S.C. 371 claiming priority to U.S. Provisional Application Ser. No. 60/871,905, filed Dec. 26, 2006. The content of the provisional application is herein incorporated by reference in its entirety for all purposes.

The present invention relates to a class of novel pyrido(3,2-d)pyrimidine derivatives. This invention also relates to pharmaceutical compositions comprising said pyrido(3,2-d)pyrimidine derivatives and one or more pharmaceutically acceptable excipients. The present invention further relates to the use of pyrido(3,2-d)pyrimidine derivatives as biologically active ingredients for manufacturing medicaments for the prevention or treatment of infection by a virus of the Flaviridae family, more specifically for inhibiting replication of hepatitis C virus.

BACKGROUND OF THE INVENTION

A huge number of pyrido(3,2-d)pyrimidine derivatives is already known in the art. For instance pyrido(3,2-d)pyrimidine derivatives with various substituents on positions 2, 4 and 6 (using the standard atom numbering for the pyrido(3,2-d)pyrimidine moiety) are known with biological activities such as competitive inhibition of pteroylglutamic acid, inhibition of thrombocyte aggregation and adhesiveness, antineoplastic activity, inhibition of dihydrofolate reductase and thymidylate synthase, e.g. from U.S. Pat. No. 2,924,599, U.S. Pat. No. 3,939,268, U.S. Pat. No. 4,460,591, U.S. Pat. No. 5,167,963 and U.S. Pat. No. 5,508,281.

Pyrido(3,2-d)pyrimidine derivatives with various substituents on positions 2, 4, 6 and 7 (using the standard atom numbering for the pyrido(3,2-d)pyrimidine moiety), some of them with biological activities, are also known e.g. from U.S. Pat. No. 5,521,190, U.S. patent application publication No. 2002/0049207, U.S. patent application publication No. 2003/0186987, U.S. patent application publication No. 2003/0199526, U.S. patent application publication No. 2004/0039000, U.S. patent application publication No. 2004/0106616, U.S. Pat. No. 6,713,484, U.S. Pat. No. 6,730,682 and U.S. Pat. No. 6,723,726.

U.S. Pat. No. 5,654,307 discloses pyrido(3,2-d)pyrimidine derivatives substituted on position 4 with monoarylamino or monobenzylamino, and on positions 6 and 7 with substituents each independently selected from the group consisting of lower alkyl, amino, lower alkoxy, mono- or dialkylamino, halogen and hydroxy. WO 01/083456 discloses pyrido(3,2-d)pyrimidine derivatives substituted on position 4 with morpholinyl and on position 2 with hydroxyphenyl or morpholinoethoxyphenyl, having PI3K and cancer inhibiting activity. U.S. Pat. No. 6,476,031 discloses substituted quinazoline derivatives, including (in reaction scheme 5) a series of pyrido (3,2-d)pyrimidine derivatives which are substituted on position 4 with hydroxy, chloro or an aryl, heteroaryl (including pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl), cycloaliphatic or cycloheteroaliphatic group being optionally spaced from the pyrido(3,2-d)pyrimidine ring by a linker such as NH. WO 02/22602 and WO 02/22607 disclose pyrazole and triazole compounds, including 2-(1-trifluoromethylphenyl)-4-fluorobenzopyrazolyl-pyrido(3,2-d)pyrimidine and 2-(1-tri-fluoromethylphenyl)-4-methyltriazolyl-pyrido (3,2-d)pyrimidine being useful as protein kinase inhibitors. WO 03/062209 discloses pyrido(3,2-d)pyrimidine derivatives substituted on position 7 with aryl or heteroaryl and on position 4 with monoarylamino or monoheteroarylamino and which may further be substituted on positions 2 and/or 6, being useful as capsaicin receptor modulators. WO 2006/069805 discloses pyrido(3,2-d)pyrimidine derivatives substituted on position 6 with aryl or heteroaryl and on both positions 2 and 4 with monoalkylamino, monocycloalkylamino, monoarylamino or monoarylalkylamino, and which may further be substituted on position 7, being useful in the treatment of a disease mediated by phosphodiesterase-4 activity. WO 2006/135993 discloses 2,4,6-trisubstituted pyrido(3,2-d)pyrimidine derivatives 2,4,6-trisubstituted useful in the treatment of hepatitis C.

However there is a continuous need in the art for specific and highly therapeutically active compounds for preventing or treating infections due to Flaviridae and pathologic conditions associated therewith, especially hepatitis C. In particular, there is a need in the art to provide drugs which are active against hepatitis C in a minor dose in order to replace existing drugs having significant side effects and to decrease treatment costs.

Hepatitis is an inflammation of the liver that is most often caused by infection with one of three viruses known as hepatitis A, B or C. Hepatitis A virus (HAV) infection is the most common cause of acute hepatitis, and usually resolves spontaneously after several weeks of acute symptoms. Hepatitis B virus (HBV) and hepatitis C virus (HCV) are the most common viral causes of chronic hepatitis, usually defined as liver inflammation persisting for more than six months. HCV is the second most common cause of viral hepatitis in general and most common cause of chronic hepatitis. The World Health Organization estimates that worldwide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1-5% of whom may develop liver cancer during the next ten years. The 15% to 45% of persons with acute hepatitis C who do recover are not subject to long-term complications and do not need treatment. Since HCV and pestiviruses belong to the same virus family and share many similarities (such as, but not limited to, organisation of the genome, analogous gene products and replication cycle), pestiviruses may be adopted as a model virus and surrogate for HCV. For example the Bovine Viral Diarrhea Virus (BVDV) is closely related to hepatitis C virus (HCV) and may be used as a surrogate virus in drug development for HCV infection.

HCV is a representative and highly significant member of the Flaviviridae family, a family of positive-strand RNA viruses. This family includes the following genera: Genus Flavivirus (type species Yellow fever virus; others include West Nile virus and Dengue Fever), Genus Hepacivirus (type species Hepatitis C virus), and Genus Pestivirus (type species Bovine viral diarrhea virus (BVDV); others include classical swine fever or hog cholera). Contrary to other families of positive strand RNA viruses such as human immunodeficiency virus (HIV), HCV seems incapable of integrating into the host's genome. The primary immune response to HCV is mounted by cytotoxic T lymphocytes. Unfortunately, this process fails to eradicate infection in most people; in fact, it may contribute to liver inflammation and, ultimately, tissue necrosis. The ability of HCV to escape immune surveillance is the subject of much speculation. One likely means of viral persistence relies on the presence of closely related but heterogeneous populations of viral genomes. Further studies of these quasi-species enable classification of several genotypes and subtypes, which have clinical implications.

The diagnosis of hepatitis C is rarely made during the acute phase of the disease because the majority of people infected experience no symptoms during this phase of the disease. Those who do experience acute phase symptoms are rarely ill enough to seek medical attention. The diagnosis of chronic phase hepatitis C is also challenging due to the absence or lack of specificity of symptoms until advanced liver disease develops, which may not occur until decades into the disease.

Hepatitis C testing begins with serological blood tests used to detect antibodies to HCV. Anti-HCV antibodies can be detected in about 80% of patients within 15 weeks after exposure, in more than 90% of patients within 5 months after exposure, and in more than 97% of patients by 6 months after exposure. Overall, HCV antibody tests have a strong positive predictive value for exposure to the hepatitis C virus, but may miss patients who have not yet developed antibodies (seroconversion), or have an insufficient level of antibodies to detect. Anti-HCV antibodies indicate exposure to the virus, but cannot determine if ongoing infection is present. All persons with positive anti-HCV antibody tests must undergo additional testing for the presence of the hepatitis C virus itself to determine whether current infection is present. The presence of HCV may be tested by using molecular nucleic acid testing methods such as, but not limited to, polymerase chain reaction (PCR), transcription mediated amplification (TMA), or branched DNA amplification. All HCV nucleic acid molecular tests have the capacity to detect not only whether the virus is present, but also to measure the amount of virus present in the blood (the HCV viral load). The HCV viral load is an important factor in determining the probability of response to interferon-base therapy, but does not indicate disease severity nor the likelihood of disease progression.

The goal of treatment is to prevent complications of HCV infection. This is principally achieved by eradication of infection. Accordingly, treatment responses are frequently characterized by the results of HCV RNA testing. Infection is considered eradicated when there is a sustained virologic response (SVR), defined as the absence of HCV RNA in serum by a sensitive test at the end of treatment and 6 months later. Persons who achieve an SVR almost always have a dramatic earlier reduction in the HCV RNA level, referred to as an early virologic response (EVR). Continued absence of detectable virus at termination of treatment is referred to as end of treatment response (ETR). A patient is considered relapsed when HCV RNA becomes undetectable on treatment but is detected again after discontinuation of treatment. Persons in whom HCV RNA levels remain stable on treatment are considered as non-responders, while those whose HCV RNA levels decline but remain detectable are referred to as partial responders.

Current standard of care for HCV treatment is a combination of (pegylated) interferon alpha and the antiviral drug ribavirin for a period of 24 or 48 weeks, depending upon the viral genotype. Should treatment with pegylated ribavirin-interferon not return a viral load reduction after 12 weeks, the chance of treatment success is less than 1%. Current indication for treatment includes patients with proven hepatitis C virus infection and persistent abnormal liver function tests. SVR of 75% or better occur in people with genotypes HCV 2 and 3 within 24 weeks of treatment, about 50% in those with genotype 1 within 48 weeks of treatment and 65% for those with genotype 4 within 48 weeks of treatment. About 80% of hepatitis C patients in the United States exhibit genotype 1, whereas genotype 4 is more common in the Middle East and Africa.

Best results have been achieved with the combination of weekly subcutaneous injections of long-acting peginterferon alpha and oral ribavirin daily. Interferons are substances naturally released by cells in the body after viral invasion. Interferon alfa-2b and peginterferon alfa-2b are synthetic versions of these substances. The protein product is manufactured by recombinant DNA-technology. Second generation interferons are further derivatized by binding to inert polyethylene glycol, thereby altering the pharmacokinetic properties. Ribavirin is a nucleoside analogue, which disrupts viral replication of hepatitis C virus (HCV).

The most common side effects of HCV treatment with (pegylated) interferon include: a decrease in white blood cells and platelets, anemia, nausea, diarrhea, fever, chills, muscle and joint pain, difficulty in concentrating, thyroid dysfunction, hair loss, sleeplessness, irritability, mild to serious depression, and rarely, suicidal thoughts. Other serious adverse events include bone marrow toxicity, cardiovascular disorders, hypersensitivity, endocrine disorders, pulmonary disorders, colitis, pancreatitis, and opthalmologic disorders (eye and vision problems). (Pegylated) interferon may also cause or make worse fatal or life-threatening neuropsychiatric, autoimmune, ischemic, and infectious disorders. Patients with persistently severe or worsening signs or symptoms of these conditions are advised to stop therapy.

The most common side effect of HCV treatment with ribavirin is anaemia, which can be treated with erythropoietin. Other side effects include mood swings, irritability, anxiety, insomnia, abdominal pain, nervousness, breathlessness, rash, hair loss, dry skin, nausea, diarrhea, loss of appetite, dizziness and weight loss. Ribavirin can also cause birth defects. Ribavirin should not be taken in combination with certain HIV drugs such as, but not limited to, didanosine, since lactic acidosis with fatal hepatic steatosis (fatty liver) may occur. Special attention should be taken for treatment with HIV co-infection.

Although the liver is the primary target of infection, studies to better define the steps of HCV infection are greatly hampered by the lack of a suitable animal model for such studies. The recent development of sub-genomic HCV RNA replicons capable of autonomous replication in the human hepatoma cell line, Huh-7, has been a significant advance in the study of HCV biology. The sub-genomic HCV RNA replicon system provides a cell-based assay to evaluate inhibitors of HCV enzymes like the protease, helicase, and RNA-dependant RNA polymerase or to evaluate nucleic acid targeting strategies like antisense RNA and ribozymes.

Targets for HCV Drug development include HCV-encoded enzymes, namely, NS2-3 and NS3-4A proteases, NS3 helicase, and NS5B RNA dependant RNA polymerase. Alternatively, HCV replication can be inhibited by blocking other HCV-encoded proteins such as NS5A or by the conserved RNA elements employing a nucleic acid based approach including antisense oligonucleotides, ribozymes, RNA aptamers, RNA decoys, and RNA interference. A major drawback for such nucleic acid based approaches is the size and charge of the nucleic acids, and their usually low physiological stability that do not allow for oral administration. Another target option for therapy is by blocking viral entry into the cell by obstruction of binding to HCV receptors such as, but not limited to, CD 209L and L-SIGN.

There is a strong need in the art to improve, or to provide alternatives to, the existing prophylactic or therapeutic solutions to infections by a virus of the Flaviridae family, more specifically HCV infection. In particular there is still a need in the art for providing alternative synthetic molecules having significant HCV replication inhibiting activity. There is also a need in the art for providing effective inhibiting molecules which are free from the significant drawbacks of the current drugs like pegylated interferon and ribavirin. Meeting these various needs in the art constitutes the main goal of the present invention.

SUMMARY OF THE INVENTION

The present invention is based on the unexpected finding that certain specific combinations of substituents on positions 2, 4 and 6 of the pyrido(3,2-d)pyrimidine core structure (using the atom numbering resulting from standard nomenclature) which are not suggested by the available prior art are however able to meet one or more of the needs recited herein above, in particular to achieve derivatives having desirable pharmacological properties such as an activity against infection by a virus of the Flaviridae family, more particularly a significant HCV replication inhibiting activity.

Based on this finding the present invention relates, in a first embodiment, to a class of pyrido(3,2-d)pyrimidine derivatives represented by the structural formula (I):

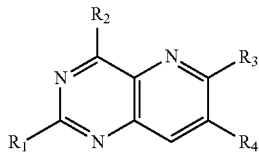

wherein:
$R_1$ is amino;
$R_2$ is selected from the group consisting of N-morpholinyl, N-thiomorpholinyl, N-thiomorpholinyl dioxide, mono-$C_{2-6}$alkyl amino wherein said $C_{2-6}$alkyl is optionally substituted with methylsulfonyl or $C_{1-4}$ alkoxy; $C_{1-6}$ alkoxy-$C_{1-6}$ alkoxy; $C_{1-6}$ alkoxy wherein said $C_{1-6}$ alkoxy is optionally substituted with a substituent selected from the group consisting of halogen and heterocyclic-oxy;
$R_4$ is hydrogen;
$R_3$ is selected from the group consisting of halogen, mono-substituted aryl groups and disubstituted aryl groups, wherein at least one substituent of said aryl group is selected from the group consisting of —CONHR$_5$, —NHCOR$_6$, —NHSO$_2$R$_7$, —NH-Het$^1$ and Het$^2$; cyclopropylcarbamoylthien-2-yl, —NH-Het$^1$ and Het$^2$;
$R_5$ is selected from the group consisting of $C_{3-10}$ cycloalkyl; $C_{1-6}$ alkyl wherein said $C_{1-6}$ alkyl is optionally substituted with one or more substituents independently selected from the group consisting of amino, alkylamino, dialkylamino, halogen, cyano and non-aromatic heterocyclic groups; $C_{1-6}$ alkoxy; heterocyclic groups wherein said heterocyclic group is optionally substituted with $C_{1-6}$ alkyl; and phenyl optionally substituted with halogen;
$R_6$ and $R_7$ are each independently selected from the group consisting of $C_{1-6}$ alkyl, wherein said $C_{1-6}$ alkyl is optionally substituted with one or more substituents selected from the group consisting of amino, halogen and hydroxyl; halogen; $C_{1-6}$ alkoxy; heterocyclic groups wherein said heterocyclic group is optionally substituted with one or more substituents selected from the group consisting of $C_{1-6}$ alkyl, acylamino and oxo; $C_{3-10}$ cycloalkyl, wherein said $C_{3-10}$ cycloalkyl is optionally substituted with amino or hydroxyl; and aryl groups, wherein said aryl group is optionally substituted with $C_{1-6}$ alkyl;
Het$^1$ is a heterocyclic group;
Het$^2$ is a N-containing heterocyclic group optionally substituted with oxo or $C_{1-6}$ alkyl or amino;
or a pharmaceutical acceptable addition salt thereof or a stereochemical isomeric form thereof or a N-oxide thereof or a solvate thereof or a pro-drug thereof.

Within this first embodiment, the present invention relates to a sub-group of tri-substituted pyrido(3,2-d)pyrimidines represented by the structural formula (I), in particular wherein $R_3$ is halogen, which are useful as intermediates for making biologically-active pyrido(3,2-d)pyrimidine derivatives.

In a second embodiment, the present invention relates to the unexpected finding that desirable pharmacological properties such as an antiviral activity, especially against infection by a virus of the Flaviridae family, more specifically the ability to inhibit hepatitis C virus (HCV) replication, is present in a sub-group of compounds represented by the structural formula (I) with the proviso that $R_3$ is not halogen.

As a consequence, the invention relates to the manufacture of pharmaceutical compositions comprising one or more pharmaceutically acceptable carriers and, as a biologically active principle, a therapeutically effective amount of at least one pyrido(3,2-d)pyrimidine derivative represented by the structural formula (I), with the proviso that $R_3$ is not halogen, and/or a pharmaceutically acceptable addition salt thereof and/or a stereochemical isomeric form thereof and/or a N-oxide thereof and/or a solvate thereof and/or a pro-drug thereof.

As a result of their biological properties mentioned hereinabove, compounds represented by the structural formula (I), with the proviso that $R_3$ is not halogen, are highly active anti-flaviridae agents, especially anti-HCV agents which, together with one or more pharmaceutically acceptable carriers, may be formulated into pharmaceutical compositions for the prevention or treatment of pathologic conditions such as, but not limited to, hepatitis C infection. It has furthermore been surprisingly found that their activity is virus-specific.

In a further embodiment, the present invention relates to combined preparations containing at least one compound of the structural formula (I), with the proviso that $R_3$ is not halogen, and one or more antiviral agents, especially one or more other anti-flaviridae agents. In a further embodiment, the present invention relates to the prevention or treatment of the above-cited pathologic conditions or infections by administering to the patient in need thereof a therapeutically effective amount of a compound represented by the structural formula (I), with the proviso that $R_3$ is not halogen, optionally in the form of a pharmaceutical composition or a combined preparation with one or more other suitable drugs, in particular antiviral agents.

In another embodiment, the present invention relates to various processes and methods for making the novel pyrido(3,2-d)pyrimidine derivatives defined by the structural formula (I) as well as their pharmaceutically acceptable salts, N-oxides, solvates, pro-drugs and/or stereochemical isomeric forms, e.g. via one or more groups of tri-substituted pyrido(3,2-d)pyrimidine intermediates.

DEFINITIONS

Figure 1:
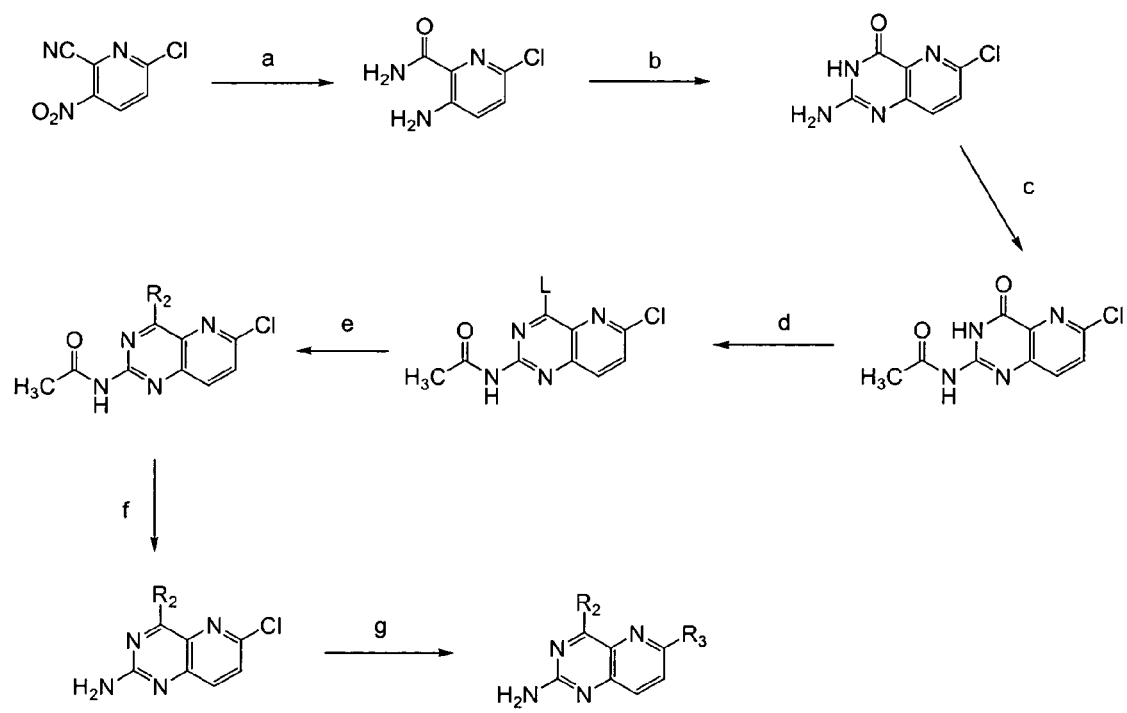
FIG. 1 schematically shows a first method for making 2,4,6-tri-substituted pyrido(3,2-d)pyrimidine derivatives represented by the formula (I) wherein the substituent in position 2 is amino, as well as intermediates therefor wherein the substituent in position 2 is a N-protected amino such as acylamino and/or wherein the substituent in position 4 is hydroxy, chloro or triazolyl.

Unless otherwise stated herein, the term "tri-substituted" means that three of the carbon atoms being in positions 2, 4 and 6 of the pyrido(3,2-d)pyrimidine core structure (according to standard atom numbering for the pyrido(3,2-d)pyrimidine moiety) are substituted with an atom or group of atoms other than hydrogen.

As used herein with respect to a substituting radical, and unless otherwise stated, the term "$C_{1-4}$ alkyl" means straight and branched chain saturated acyclic hydrocarbon monovalent radicals having from 1 to 6 carbon atoms such as, for example, methyl, ethyl, propyl, n-butyl, 1-methylethyl (isopropyl), 2-methylpropyl (isobutyl), 1,1-dimethylethyl (tert-butyl), 2-methylbutyl, n-pentyl, dimethylpropyl, n-hexyl, 2-methylpentyl, 3-methylpentyl, and the like. By analogy, the term "$C_{1-4}$ alkyl" refers to such radicals having from 1 to 4 carbon atoms.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific kind of "acyl" group within the scope of the above definition refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl and sulfonyl groups originating from aliphatic or cycloaliphatic monocarboxylic acids are designated herein as aliphatic or cycloaliphatic acyl and sulfonyl groups and include, but are not limited to, the following:
  alkanoyl (for example formyl, acetyl, propionyl, butyryl, isobutyryl, valeryl, isovaleryl, pivaloyl and the like);
  cycloalkanoyl (for example cyclobutanecarbonyl, cyclopentanecarbonyl, cyclo-hexanecarbonyl, 1-adamantanecarbonyl and the like);
  cycloalkyl-alkanoyl (for example cyclohexylacetyl, cyclopentylacetyl and the like);
  alkenoyl (for example acryloyl, methacryloyl, crotonoyl and the like);
  alkylthioalkanoyl (for example methylthioacetyl, ethylthioacetyl and the like);
  alkanesulfonyl (for example mesyl, ethanesulfonyl, propanesulfonyl and the like);
  alkoxycarbonyl (for example methoxycarbonyl, ethoxycarbonyl, propoxycarbonyl, isopropoxycarbonyl, butoxycarbonyl, isobutoxycarbonyl and the like);
  alkylcarbamoyl (for example methylcarbamoyl and the like);
  (N-alkyl)-thiocarbamoyl (for example (N-methyl)-thiocarbamoyl and the like);
  alkylcarbamidoyl (for example methylcarbamidoyl and the like); and
  alkoxyalkyl (for example methoxyalkyl, ethoxyalkyl, propoxyalkyl and the like);

Acyl and sulfonyl groups may also originate from aromatic monocarboxylic acids and include, but are not limited to, the following:
  aroyl (for example benzoyl, toluoyl, xyloyl, 1-naphthoyl, 2-naphthoyl and the like);
  arylalkanoyl (for example phenylacetyl and the like);
  arylalkenoyl (for example cinnamoyl and the like);
  aryloxyalkanoyl (for example phenoxyacetyl and the like);
  arylthioalkanoyl (for example phenylthioacetyl and the like);
  arylaminoalkanoyl (for example N-phenylglycyl, and the like);
  arylsulfonyl (for example benzenesulfonyl, toluenesulfonyl, naphthalene sulfonyl and the like);
  aryloxycarbonyl (for example phenoxycarbonyl, naphthyloxycarbonyl and the like);
  arylalkoxycarbonyl (for example benzyloxycarbonyl and the like);
  arylcarbamoyl (for example phenylcarbamoyl, naphthylcarbamoyl and the like);
  arylglyoxyloyl (for example phenylglyoxyloyl and the like);
  arylthiocarbamoyl (for example phenylthiocarbamoyl and the like); and
  arylcarbamidoyl (for example phenylcarbamidoyl and the like).

Acyl groups may also originate from an heterocyclic monocarboxylic acids and include, but are not limited to, the following:
  heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and
  heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneacetyl, furylacetyl, imidazolylpropionyl, tetrazolylacetyl, 2-(2-amino-4-thiazolyl)-2-methoxyiminoacetyl and the like).

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclo-propyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenanthracyl, fluoranthenyl, chrysenyl, pyrenyl, biphenyyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting radical, and unless otherwise stated, the term "heterocyclic" means a mono- or polycyclic, saturated or mono-unsaturated or poly-unsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzodioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindolyl, naphthotriazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyi, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, pheno-metoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-6}$ alkyl (optionally containing one or more functions or radicals selected from the group consisting of oxo, hydroxyl, ether, amino, cyano, nitro, formyl and hydroxylamino; depending upon the number of unsaturations in the 3 to 10 atoms ring, heterocyclic radicals are conventionally sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-6}$ alkyl, $C_{3-10}$ cycloalkyl and aryl.

As used herein with respect to a substituting radical, and unless otherwise stated, the terms "$C_{1-6}$ alkoxy" and "heterocyclic-oxy" refer to substituents wherein a carbon atom of a $C_{1-6}$ alkyl or heterocyclic radical (each of them such as defined herein), is attached to an oxygen atom through a single bond such as, but not limited to, methoxy, ethoxy, propoxy, butoxy, pentoxy, isopropoxy, sec-butoxy, tert-butoxy, isopentoxy, and various isomers of piperidinoxy, methylpiperidinoxy, pyrrolidinoxy, pyridinoxy, tetrahydrofuranyloxy, and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "arylalkyl" refers to an aliphatic saturated hydrocarbon monovalent radical (preferably a $C_{1-6}$ alkyl radical such as defined above) onto which an aryl radical (such as defined above) is attached via a carbon atom, and wherein the said aliphatic radical and/or the said aryl radical may be optionally substituted with one or more substituents independently selected from the group consisting of halogen, amino, hydroxyl, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, and the like.

As used herein with respect to a substituting radical, and unless otherwise stated, the term "alkylamino" means that one (thus monosubstituted amino) or respectively two (thus disubstituted amino) $C_{1-6}$ alkyl radical(s) (as defined herein, respectively, is/are attached to a nitrogen atom through a single bond such as, but not limited to, methylamino, dimethylamino, ethylamino, diethylamino, isopropylamino, n-butylamino, tert-butylamino, dibutylamino.

As used herein and unless otherwise stated, the term "stereochemical isomeric form" refers to all possible different isomeric as well as conformational forms which the compounds represented by the formula (I) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a pyrido(3,2-d)pyrimidine derivative of this invention with a suitable inorganic solvent (e.g. hydrates) or organic solvent, such as but not limited to alcohols, ketones, esters, ethers, nitriles and the like.

DETAILED DESCRIPTION OF THE INVENTION

In a first embodiment of the present invention, the novel trisubstituted pyrido(3,2-d)pyrimidine derivatives are as defined in the structural formula (I), wherein each of the substituents $R_1$, $R_2$, $R_3$, $R_4$, $R_5$, $R_6$ and/or $R_7$ may independently correspond to any of the definitions given above, in particular with any of the individual species listed therein or with any particular meaning (such as illustrated above) of generic terms used for naming or designating substituting groups such as, but not limited to, "$C_{1-6}$ alkyl", "$C_{3-10}$ cycloalkyl", "aryl", "heterocyclic", "halogen", "arylalkyl", "alkylamino", "$C_{1-6}$ alkoxy" and the like.

Within the broad class of trisubstituted pyrido(3,2-d)pyrimidine derivatives represented by the structural formula (I), a useful sub-group of compounds is one wherein $R_3$ is a monosubstituted phenyl group, wherein the substituent of said phenyl group is located in para position with respect to the pyrido (3,2-d)pyrimidinyl core.

Within the broad class of trisubstituted pyrido(3,2-d)pyrimidine derivatives represented by the structural formula (I), a useful sub-group of compounds is one wherein $R_3$ is a monosubstituted phenyl group substituted with —CONHR$_5$, and wherein $R_5$ is selected from the group consisting of cyclopropyl, cyclopentyl, cyclohexyl, n-butyl, isobutyl, tert-butyl, isopropyl, n-propyl, ethyl and methyl.

Within the broad class of trisubstituted pyrido(3,2-d)pyrimidine derivatives represented by the structural formula (I), a useful sub-group of compounds is one wherein $R_3$ is a monosubstituted phenyl group substituted with —CONHR$_5$, and wherein $R_5$ is $C_{2-4}$ alkyl optionally substituted with one to three substituents independently selected from the group consisting of dimethylamino, fluoro, pyrrolidinyl and morpholinyl.

Within the broad class of trisubstituted pyrido(3,2-d)pyrimidine derivatives represented by the structural formula (I), a useful sub-group of compounds is one wherein $R_3$ is a monosubstituted phenyl group substituted with —NHCOR$_6$, wherein $R_6$ is cyclopropyl, isopropyl or ethyl, and wherein said $R_6$ is optionally substituted with amino and/or hydroxyl.

Within the broad class of trisubstituted pyrido(3,2-d)pyrimidine derivatives represented by the structural formula (I), a useful sub-group of compounds is one wherein $R_3$ is a di-substituted phenyl group wherein one second substituent of said phenyl group is halogen, especially fluoro.

Within the broad class of trisubstituted pyrido(3,2-d)pyrimidine derivatives represented by the structural formula (I), a useful sub-group of compounds is one wherein $R_3$ is a monosubstituted phenyl group, wherein the substituent of said phenyl group is located in meta position with respect to the pyrido(3,2-d)pyrimidinyl core.

Within the broad class of trisubstituted pyrido(3,2-d)pyrimidine derivatives represented by the structural formula (I), a useful sub-group of compounds is one wherein $R_3$ is a monosubstituted phenyl group substituted with a N-containing heterocyclic group Het$^2$, said Het$^2$ being attached to said phenyl group either through a nitrogen atom or through a carbon atom, and said Het$^2$ being optionally substituted with oxo or methyl.

Within the broad class of trisubstituted pyrido(3,2-d)pyrimidine derivatives represented by the structural formula (I), a useful sub-group of compounds is one wherein $R_3$ is a monosubstituted phenyl group substituted with —NH-Het$^1$ wherein said Het$^1$ is attached to the adjacent nitrogen atom through a carbon atom, e.g. Het$^1$ may be, but is not limited to, thiadiazol-2-yl or thiazol-2-yl.

Within the broad class of trisubstituted pyrido(3,2-d)pyrimidine derivatives represented by the structural formula (I), a useful sub-group of compounds is one wherein $R_3$ is a monosubstituted phenyl group substituted with —CONHR$_5$, and wherein $R_5$ is a heterocyclic group preferably attached to the adjacent nitrogen atom through a carbon atom, e.g. $R_5$ may be, but is not limited to, piperidinyl.

Within the broad class of trisubstituted pyrido(3,2-d)pyrimidine derivatives represented by the structural formula (I), a useful sub-group of compounds is one wherein $R_3$ is a monosubstituted phenyl group substituted with —CONHR$_5$, and wherein $R_5$ is a N-containing heterocyclic group Het$^2$, said Het$^2$ being preferably attached to the adjacent nitrogen atom through a carbon atom and being optionally substituted with $C_{1-6}$ alkyl, e.g. $R_5$ may be, but is not limited to, methylpiperidinyl, ethylpiperidinyl or isopropylpiperidinyl.

Within the broad class of trisubstituted pyrido(3,2-d)pyrimidine derivatives represented by the structural formula (I), a useful sub-group of compounds is one wherein $R_3$ is a monosubstituted phenyl group substituted with a N-containing heterocyclic group Het$^2$, wherein Het$^2$ is attached to said phenyl group through a nitrogen atom or, preferably, through a carbon atom and is optionally substituted with amino or methyl, e.g. Het$^1$ may be, but is not limited to, triazol-3-yl, thiazol-2-yl, methyltriazol-3-yl, methylthiazol-2-yl, aminotriazol-3-yl or aminothiazol-2-yl.

Within the broad class of trisubstituted pyrido(3,2-d)pyrimidine derivatives represented by the structural formula (I), a useful sub-group of compounds is one wherein $R_3$ is a monosubstituted phenyl group substituted with —CONHR$_5$, wherein the substituent of said phenyl group is located in para position with respect to the pyrido(3,2-d)pyrimidinyl core and wherein $R_5$ is selected from the group consisting of cyclopropyl, cyclopentyl, cyclohexyl, n-butyl, isobutyl, tert-butyl, isopropyl, n-propyl, ethyl and methyl.

Within the broad class of trisubstituted pyrido(3,2-d)pyrimidine derivatives represented by the structural formula (I), a useful sub-group of compounds is one wherein $R_3$ is a mono-substituted phenyl group substituted with —$NHCOR_6$, wherein the substituent of said phenyl group is located in para position with respect to the pyrido(3,2-d)pyrimidinyl core and wherein $R_6$ is cyclopropyl, isopropyl or ethyl, and wherein said $R_6$ is optionally substituted with amino and/or hydroxyl.

Within the broad class of trisubstituted pyrido(3,2-d)pyrimidine derivatives represented by the structural formula (I), a useful sub-group of compounds is one wherein $R_3$ is a di-substituted phenyl group, wherein one substituent of said phenyl group is located in para position with respect to the pyrido(3,2-d)pyrimidinyl core, and wherein one substituent is halogen.

$R_3$ is a mono-substituted phenyl group substituted with a N-containing heterocyclic group $Het^2$ attached to said phenyl group through a nitrogen atom, wherein said substituent of the phenyl group is located in para position with respect to the pyrido(3,2-d)pyrimidinyl core.

Within the broad class of trisubstituted pyrido(3,2-d)pyrimidine derivatives represented by the structural formula (I), a useful sub-group of compounds is one wherein $R_3$ is a mono-substituted phenyl group substituted with —NH-$Het^1$, wherein the substituent of said phenyl group is located in para position with respect to the pyrido(3,2-d)pyrimidinyl core, and wherein said $Het^1$ is attached to nitrogen through a carbon atom.

Within the broad class of trisubstituted pyrido(3,2-d)pyrimidine derivatives represented by the structural formula (I), a useful sub-group of compounds is one wherein $R_3$ is a mono-substituted phenyl group substituted with —$CONHR_5$, wherein the substituent of said phenyl group is located in para position with respect to the pyrido(3,2-d)pyrimidinyl core and wherein $R_5$ is a heterocyclic attached to nitrogen through a carbon atom.

Within the broad class of trisubstituted pyrido(3,2-d)pyrimidine derivatives represented by the structural formula (I), a useful sub-group of compounds is one wherein $R_3$ is a mono-substituted phenyl group substituted with a N-containing heterocyclic group $Het^2$, wherein the substituent of said phenyl group is located in para position with respect to the pyrido(3,2-d)pyrimidinyl core, wherein $Het^2$ is attached to said phenyl group through a nitrogen atom or a carbon atom.

Within the broad class of trisubstituted pyrido(3,2-d)pyrimidine derivatives represented by the structural formula (I), a useful sub-group of compounds is one wherein $R_6$ is selected from the group consisting of $C_{1-6}$ alkyl, wherein said $C_{1-6}$ alkyl is optionally substituted with one or more substituents selected from the group consisting of amino, halogen and hydroxyl; $C_{1-6}$ alkoxy; nitrogen-containing heterocyclic groups; $C_{3-10}$ cycloalkyl, wherein said $C_{3-10}$ cycloalkyl is optionally substituted with amino or hydroxyl.

Within the broad class of trisubstituted pyrido(3,2-d)pyrimidine derivatives represented by the structural formula (I), a useful sub-group of compounds is one wherein $R_7$ is selected from the group consisting of $C_{3-10}$ cycloalkyl; $C_{1-6}$ alkyl, wherein said $C_{1-6}$ alkyl is optionally substituted with halogen; aryl groups, wherein said aryl group is optionally substituted with $C_{1-6}$ alkyl; heterocyclic groups, wherein said heterocyclic group is optionally substituted with one or more substituents selected from the group consisting of $C_{1-6}$ alkyl, acylamino and oxo.

The present invention further provides various processes and methods for making the novel pyrido(3,2-d)pyrimidine derivatives having the structural formula (I). As a general rule, the preparation of these compounds is based on the principle that, starting from a suitable pyrido(3,2-d)pyrimidine precursor (usually a 2,3,6-trisubstituted pyridine, method shown in FIG. 1) or from 2-amino-4-hydroxy-6-chloro-pyrido(3,2-d)pyrimidine (method shown in FIG. 2), each of the desirable substituents $R_2$ and $R_3$ may be introduced separately without adversely influencing the presence of one or more substituents already introduced at other positions on the pyrido(3,2-d)pyrimidine moiety or the capacity to introduce further substituents later on.

Methods of manufacture have been developed by the present inventors which may be used alternatively to, or may be combined with, the methods of synthesis already known in the art of pyrido(3,2-d)pyrimidine derivatives (depending upon the targeted final compound). For instance, the synthesis of mono- and di-N-oxides of the pyrido(3,2-d)pyrimidine derivatives of this invention can easily be achieved by treating the said derivatives with an oxidizing agent such as, but not limited to, hydrogen peroxide (e.g. in the presence of acetic acid) or a peracid such as chloroperbenzoic acid. The methods for making the pyrido(3,2-d)pyrimidine derivatives of the present invention will now be explained in more details by reference to the appended FIGS. 1 and 2 wherein, unless otherwise stated hereinafter, each of the substituting groups or atoms $R_2$, $R_3$, $R_4$ and $R_1$ is as defined in formula (I) of the summary of the invention and, more specifically, may correspond to any of the individual meanings disclosed above.

In the description of the reaction steps involved in each figure, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

FIG. 1 schematically shows a first method for making 2-amino-4,6-di-substituted pyrido(3,2-d)pyrimidine derivatives represented by the structural formula (I) through a series of intermediates. In step (a), the 3-nitro group of 6-chloro-2-cyano-3-nitropyridine is reduced, either catalytically (e.g. by using platinum or palladium under an atmosphere of hydrogen) or chemically (e.g. by using iron or tin under acidic conditions) and at the same time the 2-cyano group is hydrolyzed into a carboxamide function. A ring closure reaction leading to the formation of the pyrido[3,2-d]pyrimidine scaffold occurs in step (b) by treatment of 6-chloro-2-carboxamido-3-aminopyridine with a ring closure reagent such as, but not limited to, chloro-formamidine or guanidine. In step (c), the amino group at position 2 is protected, for example by means of an acyl group such as a pivaloyl group (not shown in FIG. 1) or acetyl group, by reaction with acetic anhydride or pivaloyl anhydride in pyridine as a solvent, thus resulting into the introduction of a N-protected amino group at position 2 such as, but not limited to, acetamido (shown in FIG. 1) or pivalamido. Activation of the tautomeric hydroxyl group at position 4 of the pyrido[3,2-d]pyrimidine scaffold for the subsequent nucleophilic displacement reaction occurs in step (d) by preparing the corresponding 4-(1,2,4-triazolyl)-pyrido [3,2-d]pyrimidine derivative or 4-chloro-pyrido[3,2-d]pyrimidine derivative. The 4-triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The chlorine atom or triazolyl group is designated as L in FIG. 1. Nucleophilic displacement of the triazolyl group or chlorine atom occurs in step (e) by reaction with an appropriate nucleophile having the general formula $R_2H$, wherein $R_2$ is as defined in the general formula (I), in a polar aprotic solvent. Examples of suitable nucleophiles are sodium or potassium $C_{1-6}$ alkoxides, and primary alkylamines or heterocyclic amines such as morpholine, thiomorpholine and thiomorpholine oxide. In step (f), the amino protecting group is cleaved off by using standard cleavage conditions such as acidic or basic hydrolysis. In the last step (g), the 2-amino-4-$R_2$-substituted-6-chloro-pyrido(3,2-d)pyrimidine derivative is subjected to a palladium-catalyzed reaction such as, but not limited to, a Suzuki reaction with a suitable aryl-boronic acid, or a pinacol ester thereof, i.e. wherein the aryl group includes the relevant substituent(s), to yield the desired derivative represented by the structural formula (I).

Figure 2:
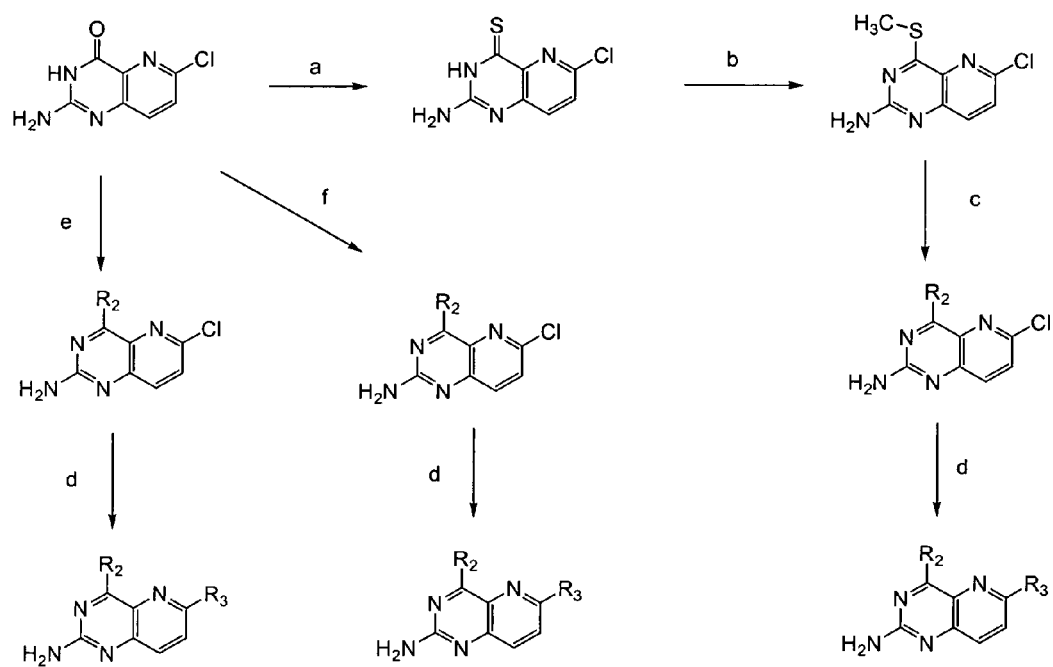
FIG. 2 schematically shows a second method for making 2,4,6-tri-substituted pyrido(3,2-d)pyrimidine derivatives represented by the formula (I) wherein the substituent in position 2 is amino, as well as intermediates therefor wherein the substituent in position 4 is sulfhydryl or methylthio.

FIG. 2 shows a second method for making 2-amino-4,6-di-substituted pyrido(3,2-d)pyrimidine derivatives represented by the structural formula (I). In step (a), the tautomeric hydroxyl group at position 4 of the pyrido(3,2-d)pyrimidine scaffold is converted to the corresponding 4-sulfhydryl group by treatment with phosphorus pentasulfide or Lawesson's reagent. The resulting 2-amino-4-thioxo-6-chloro-pyrido(3, 2-d)pyrimidine analogue is then methylated in step (b) by treatment with iodomethane under alkaline conditions (e.g. using a 1 N NaOH solution). The thiomethyl group at position 4 is then displaced in step (c) by a nucleophile bearing the general formula $R_2H$, wherein $R_2$ is as defined in the general formula (I). Examples of suitable nucleophiles include sodium or potassium $C_{1-6}$ alkoxides, and primary alkylamines or heterocyclic amines such as morpholine, thiomorpholine and thiomorpholine oxide. Alternatively, such a group $R_2$ can also be directly introduced in step (e) at position 4 of the pyrido[3,2-d]pyrimidine scaffold by treatment of 2-amino-4-hydroxy-6-chloro-pyrido[3,2-d]pyrimidine with an appropriate primary alkylamine or heterocyclic amine in the presence of a suitable amount of 1,1,1,3,3,3-hexamethyl-disilazane as a reagent, ammonium sulphate, and p-toluene-sulfonic acid as a catalyst (the so-called silylation-amination approach). Still another method in order to introduce in one step a nucleophile at position 4 of the pyrido(3,2-d)pyrimidine scaffold is depicted in step (f). Briefly, 2-amino-4-oxo-6-chloro-pyrido[3,2-d]pyrimidine is treated with a base, such as for example 1,8-diazabicyclo[5.4.0]undec-7-ene (hereinafter referred as DBU), triethylamine or N,N-diisopropyl-ethylamine (DIPEA) in an aprotic solvent (such as, but not limited to, dimethylformamide, 1-methyl-2-pyrrolidinone, tetrahydrofuran, dichloromethane, or mixtures thereof). Subsequently, a peptide coupling agent such as, but not limited to, benzotriazol-1-yloxytris(dimethylamino)-phosphonium hexafluorophosphate (BOP), benzotriazole-1-yl-oxy-trispyr-rolidinophosphonium hexafluorophosphate (PyBOP) or bromo-tris-pyrrolidino-phosphonium hexafluorophosphate (PyBrOP) is added, followed by addition of an appropriate nucleophile. In step (d), the 2-amino-4-$R_2$-substituted-6-chloro-pyrido(3,2-d)pyrimidine derivative is subjected to a palladium-catalyzed reaction such as, but not limited to, a Suzuki reaction with a suitable aryl-boronic acid, or a pinacol ester thereof, i.e. wherein the aryl group may include one or more relevant substituent(s), to yield the trisubstituted pyrido (3,2-d)pyrimidine derivative represented by the structural formula (I).

In another particular embodiment, the invention relates to a group of trisubstituted pyrido(3,2-d)pyrimidine derivatives, as well as pharmaceutical compositions comprising such pyrido(3,2-d)pyrimidine derivatives as active principle, having the above general formula (I), and being in the form of a pharmaceutically acceptable salt. The latter include any therapeutically active non-toxic addition salt which compounds having the general formula (I), especially these wherein $R_3$ is not halogen, are able to form with a salt-forming agent. Such addition salts may conveniently be obtained by treating the trisubstituted pyrido(3,2-d)pyrimidine derivatives of the invention with an appropriate salt-forming acid or base. For instance, pyrido(3,2-d)pyrimidine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as, but not limited to, hydrohalides (e.g. hydrochloride and hydrobromide), sulfate, nitrate, phosphate, diphosphate, carbonate, bicarbonate, and the like; and organic mono- or di-acids resulting in forming salts such as, for example, acetate, propanoate, hydroxyacetate, 2-hydroxypropanoate, 2-oxo-propanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-amino-salicylate, pamoate, bitartrate, camphorsulfonate, edetate, 1,2-ethanedisulfonate, fumarate, glucoheptonate, gluconate, glutamate, hexylresorcinate, hydroxynaphtoate, hydroxyethanesulfonate, mandelate, methylsulfate, pantothenate, stearate, as well as salts derived from ethanedioic, propanedioic, butanedioic, (Z)-2-butene-dioic, (E)2-butenedioic, 2-hydroxybutanedioic, 2,3-dihydroxybutane-dioic, 2-hydroxy-1,2,3-propanetricarboxylic and cyclohexanesulfamic acids and the like.

Trisubstituted pyrido(3,2-d)pyrimidine derivatives represented by the general formula (I), especially these wherein $R_3$ is not halogen, having acidic properties may be converted in a similar manner into the corresponding therapeutically active, non-toxic base addition salt form. Examples of appropriate salt-forming bases include, for instance, inorganic bases like metallic hydroxides such as, but not limited to, those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chlorop-rocaine, choline, diethanolamine, ethylene-diamine, N-methylglucamine, procaine and the like.

Reaction conditions for treating the trisubstituted pyrido (3,2-d)pyrimidine derivatives represented by the general formula (I) of this invention with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water solubility, lower toxicity, greater stability and/or slower dissolution rate to the pyrido(3,2-d)pyrimidine derivative of this invention.

The present invention further provides the use of a trisubstituted pyrido(3,2-d)pyrimidine derivative represented by the structural formula (I), especially these wherein $R_3$ is not halogen, or a pharmaceutically acceptable salt or a solvate thereof, as a biologically-active ingredient, i.e. active principle, especially as a medicine or for the manufacture of a medicament for the treatment of a Flaviridae viral infection such as, but not limited to, hepatitis C.

The invention further relates to a pharmaceutical composition comprising:
(a) one or more pyrido(3,2-d)pyrimidine derivatives represented by the structural formula (I), wherein $R_3$ is not halogen, and
(b) one or more pharmaceutically acceptable carriers.

In one embodiment, the compounds of the present invention are used in combination with other active therapeutic ingredients or agents. Combinations of the compounds represented by Formula (I) and additional active agents may be selected to treat patients with a viral infection, e.g., HBV, HCV, or HIV infection.

Preferably, the other active therapeutic ingredients or agents preferably are interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

Combinations of the compounds represented by Formula (I) are typically selected based on the condition to be treated, cross-reactivities of ingredients and pharmaco-properties of the combination. For example, when treating an infection (e.g., HCV), the compositions of the invention may be combined with other active agents (such as those described herein).

Suitable active agents or ingredients which can be combined with the compounds represented by Formula (I) can include interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application provides pharmaceutical compositions comprising a compound of the present invention, or a pharmaceutically acceptable salt, solvate, and/or ester thereof, in combination with at least one additional active agent, and a pharmaceutically acceptable carrier or excipient.

According to the present invention, the active agent used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In another embodiment, the present application provides pharmaceutical compositions comprising a compound of the present invention, or a pharmaceutically acceptable salt, solvate, and/or ester thereof, in combination with at least one additional active agent selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application provides a combination pharmaceutical agent comprising:
a) a first pharmaceutical composition comprising a compound of the present invention, or a pharmaceutically acceptable salt, solvate, or ester thereof; and
b) a second pharmaceutical composition comprising at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

More specifically, one or more compounds of the present invention may be combined with one or more compounds selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

It is also possible to combine any compound of the invention with one or more other active agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g. 1-12 hours), by administration of a unit dose of one or more other active agents. In other cases, it may be desirable to administer a unit dose of one or more other active agents first, followed, after a period of hours (e.g. 1-12 hours), by administration of a unit dose of a compound of the invention.

The combination therapy may provide "synergy" or "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In still yet another embodiment, the present application provides for methods of inhibiting HCV polymerase in a cell, comprising: contacting a cell infected with HCV with an effective amount of a compound represented by Formula (I), or a pharmaceutically acceptable salt, solvate, and/or ester thereof, whereby HCV polymerase is inhibited.

In still yet another embodiment, the present application provides for methods of inhibiting HCV polymerase in a cell, comprising contacting a cell infected with HCV with an effective amount of a compound represented by Formula (I), or a pharmaceutically acceptable salt, solvate, and/or ester thereof, and at least one additional active agent, whereby HCV polymerase is inhibited.

In still yet another embodiment, the present application provides for methods of inhibiting HCV polymerase in a cell, comprising contacting a cell infected with HCV with an effective amount of a compound represented by Formula (I), or a pharmaceutically acceptable salt, solvate, and/or ester thereof, and at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV.

In still yet another embodiment, the present application provides for methods of treating a viral infection in a patient, comprising: administering to the patient a therapeutically effective amount of a compound represented by Formula (I), or a pharmaceutically acceptable salt, solvate, and/or ester thereof.

In still yet another embodiment, the present application provides for methods of treating a viral infection in a patient, comprising: administering to the patient a therapeutically effective amount of a compound represented by Formula (I), or a pharmaceutically acceptable salt, solvate, and/or ester thereof, and at least one additional active agent.

In still yet another embodiment, the present application provides for methods of treating HCV in a patient, comprising: administering to the patient a therapeutically effective amount of a compound represented by Formula (I), or a pharmaceutically acceptable salt, solvate, and/or ester thereof.

In still yet another embodiment, the present application provides for methods of treating HCV in a patient, comprising: administering to the patient a therapeutically effective amount of a compound represented by Formula (I), or a pharmaceutically acceptable salt, solvate, and/or ester thereof, and at least one additional active agent, whereby HCV polymerase is inhibited.

In still yet another embodiment, the present application provides for methods of treating HCV in a patient, comprising: administering to the patient a therapeutically effective amount of a compound represented by Formula (I), or a pharmaceutically acceptable salt, solvate, and/or ester thereof, and at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In still yet another embodiment, the present application provides for the use of a compound of the present invention, or a pharmaceutically acceptable salt, solvate, and/or ester thereof, for the preparation of a medicament for treating a viral infection, e.g., an HBV/HCV infection.

In yet another embodiment, the present application provides a method for treating or preventing a viral infection comprising co-administering, to a patient in need thereof, a therapeutically effective amount of at least one compound represented by Formula (I) and at least one additional active agent selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In another more specific embodiment, this invention provides combinations, preferably synergistic combinations, of one or more pyrido(3,2-d)pyrimidine derivatives represented by the general formula (I), wherein $R_3$ is not halogen, with one or more other antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of biologically desirable effects such as, but not limited to, an anti-viral activity against a Flaviridae virus, e.g. HCV.

The invention further relates to a pharmaceutical composition or combined preparation having synergistic effects against a hepatitis C infection and containing:
(a) one or more anti-viral agents, and
(b) at least one pyrido(3,2-d)pyrimidine derivative represented by the general formula (I), wherein $R_3$ is not halogen, and
(c) optionally one or more pharmaceutical excipients or pharmaceutically acceptable carriers,
for simultaneous, separate or sequential use in the treatment of HCV infection.

Suitable anti-viral agents for inclusion into the synergistic antiviral compositions or combined preparations of this invention include, for instance, ribavirin, (pegylated)interferon, and retroviral enzyme inhibitors belonging to categories well known in the art, such as HIV-1 IN inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

Especially relevant to this aspect of the invention is the inhibition of the replication of viruses selected from the group consisting of picorna-, toga-, bunya, orthomyxo-, paramyxo-, rhabdo-, retro-, arena-, hepatitis B-, hepatitis C-, hepatitis D-, adeno-, vaccinia-, papilloma-, herpes-, corona-, varicella- and zoster-virus, in particular human immunodeficiency virus (HIV). Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x + FIC_y$) is equal to 1.0, the combination is said to be additive; when it is between 1.0 and 0.5, the combination is defined as sub-synergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical composition or combined preparation with synergistic activity against viral infection according to this invention may contain the trisubstituted pyrido(3,2-d) pyrimidine derivative represented by the structural formula (I), wherein $R_3$ is not halogen, over a broad content range depending on the contemplated use and the expected effect of the preparation. The pyrido(3,2-d)pyrimidine derivative content of the combined preparation may be within a range of from about 1 to about 99% by weight, preferably from about 5 to about 95% by weight, more preferably from about 20 to 80% by weight.

The pharmaceutical compositions and combined preparations according to this invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperiteneously) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the pyrido(3,2-d) pyrimidine derivative represented by the general formula (I), wherein $R_3$ is not halogen, and optionally the additional one or more antiviral agents, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the pyrido(3,2-d)pyrimidine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphthalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered topically, in an ointment, gel or the like, or transdermally, using a conventional transdermal drug delivery system.

Since, in the case of combined preparations including a pyrido(3,2-d)pyrimidine derivative of this invention and an additional antiviral agent, both ingredients do not necessarily bring out their synergistic therapeutic effect against the pathologic condition (viral infection) directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for treating hepatitis C in a patient, preferably a mammal, more preferably a human being. The method of this invention consists of administering to the patient in need thereof an effective amount of a trisubstituted pyrido(3,2-d)pyrimidine derivative having the general formula (I), wherein $R_3$ is not halogen, optionally together with an effective amount of an antiviral agent, or a pharmaceutical composition comprising the same, such as disclosed above in extensive details. The effective amount is usually in the range of about 0.01 mg to 20 mg, preferably about 0.1 mg to 5 mg, per day per kg bodyweight for humans. Depending upon the pathologic condition to be treated and the patient's condition, the said effective amount may be divided into several sub-units per day or may be administered at more than one day intervals. The patient to be treated may be any warm-blooded animal, preferably a mammal, more preferably a human being, suffering from said pathologic condition.

The preferred compounds of the present invention are non-sedating. In other words, a dose of such compounds that is twice the minimum dose sufficient to provide analgesia in an animal model for determining pain relief causes only transient (i.e. lasting for no more than half the time that pain relief lasts) or preferably no statistically significant sedation in an animal model assay of sedation (using the method described by Fitzgerald et al. in *Toxicology* (1988) 49:433-9). Preferably, a dose that is five times the minimum dose sufficient to provide analgesia does not produce statistically significant sedation. More preferably, a compound provided herein does not produce sedation at intravenous doses of less than 10 mg/kg per day or at oral doses of less than 30 mg/kg per day. If desired, compounds provided herein may be evaluated for toxicity (a preferred compound is non-toxic when an antiviral amount is administered to a subject) and/or side effects (a preferred compound produces side effects comparable to placebo when a therapeutically effective amount of the compound is administered to a subject). Toxicity and side effects may be assessed using any standard method. In general, the term "non-toxic" as used herein shall be understood as referring to any substance that, in keeping with established criteria, is susceptible to approval by the United States Federal Drug Administration for administration to mammals, preferably humans. Toxicity may be also evaluated using assays including bacterial reverse mutation assays, such as an Ames test, as well as standard teratogenicity and tumorogenicity assays. Preferably, administration of compounds provided herein within the therapeutic dose ranges disclosed hereinabove does not result in prolongation of heart QT intervals (e.g. as determined by electrocardiography in guinea pigs, minipigs or dogs). When administered daily, such doses also do not cause liver enlargement resulting in an increase of liver to body weight ratio of more than 50% over matched controls in laboratory rodents (e.g. mice or rats). Such doses also preferably do not cause liver enlargement resulting in an increase of liver to body weight ratio of more than 10% over matched untreated controls in dogs or other non-rodent mammals.

Another embodiment of this invention includes the various precursors or "pro-drug" forms of trisubstituted pyrido(3,2-d)pyrimidine derivatives having the general formula (I), wherein $R_3$ is not halogen, of the present invention. It may be desirable, under specific circumstances, to formulate the compounds of the present invention in the form of a chemical species which itself is not significantly biologically-active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purpose of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome.

The present invention will be further described with reference to certain more specific embodiments, detailed schemes and examples, but the present invention is not limited thereto but only by the attached claims. The following examples are given by way of illustration only.

EXAMPLES 1 TO 7

Synthesis of 6-benzamido-N4-(2-methanesulfonyl-ethyl)-pyrido[3,2-d]pyrimidin-2-ylamines Various 6-benzamido-N4-(2-methanesulfonyl-ethyl)-pyrido[3,2-d]pyrimidin-2-yl-amines were synthesized according to the synthetic sequence outlined in Scheme 1.

Scheme 1

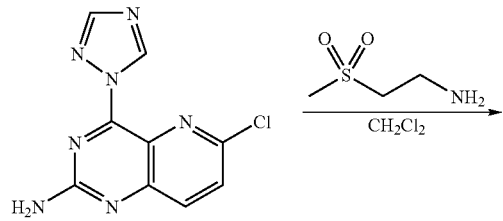

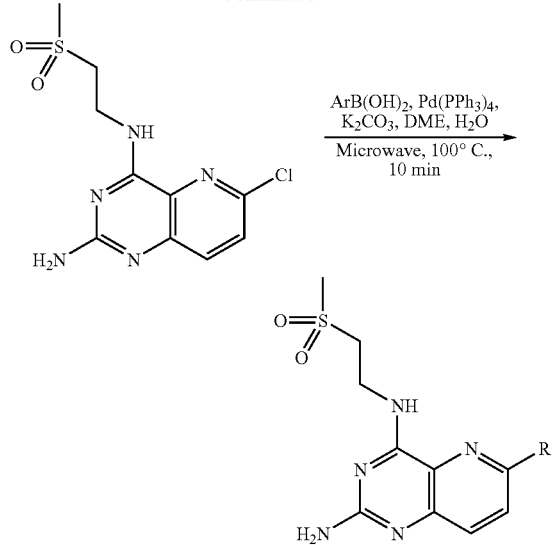

A suspension of 6-chloro-4-[1,2,4]triazol-1-yl-pyrido[3,2-d]pyrimidin-2-ylamine (0.32 g), 2-aminoethylmethylsulfone hydrochloride (0.31 g,) and DIEA (0.34 mL, 1.4 mmole) in DCM (10 mL) was stirred at room temperature for 2 days. EtOAc was added and the mixture was extracted with 5% aq LiCl solution and brine. The organic layer was dried and concentrated to provide 0.32 g of the crude product, 6-chloro-N4-(2-methanesulfonyl-ethyl)-pyrido[3,2-d]pyrimidine-2,4-diamine which, used without further purification, was characterized by its mass spectrum as follows: MS (m/z) 301.8 [M+H]+.

A mixture of 6-chloro-N4-(2-methanesulfonyl-ethyl)-pyrido[3,2-d]pyrimidine-2,4-diamine (23 mg), potassium carbonate (27 mg), tetrakis(triphenylphosphine) palladium (8 mg, 0.007 mmol) and a suitable aryl-boronic acid, or a pinacol ester thereof, (0.12 mmol) in DME (1.5 mL) and water (1 mL) was heated to 100° C. for 10 minutes under microwave irradiation. Solvents were concentrated in vacuo and the residue was purified by RP HPLC using a C18 column with a gradient of $H_2O$, 0.1% TFA-acetonitrile, to provide the desired product. This procedure provided, with yields ranging from 20% to 65% depending upon the aryl introduced at the 6-position of the pyrido[3,2-d]pyrimidine ring system, the following pure compounds which were obtained and characterized by their mass spectra as indicated in Table 1.

TABLE 1

| Example | Structure | Name | Observed Mass M + 1 |
|---|---|---|---|
| 1 | 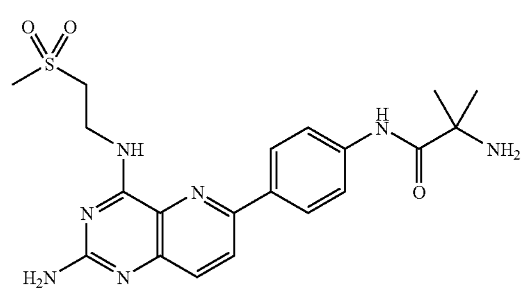 | 2-Amino-N-{4-[2-amino-4-(2-methanesulfonyl-ethylamino)-pyrido[3,2-d]pyrimidin-6-yl]-phenyl}-2-methyl-propionamide | 444.2 |

TABLE 1-continued

| Example | Structure | Name | Observed Mass M + 1 |
|---|---|---|---|
| 2 | 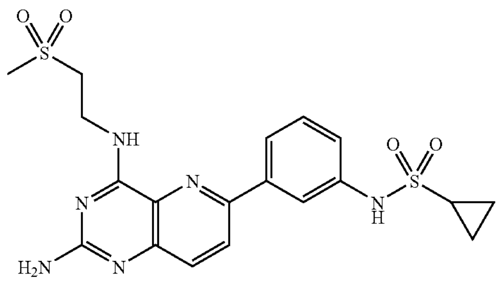 | Cyclopropanesulfonic acid {3-[2-amino-4-(2-methanesulfonyl-ethylamino)-pyrido[3,2-d]pyrimidin-6-yl]-phenyl}-amide | 463.1 |
| 3 | 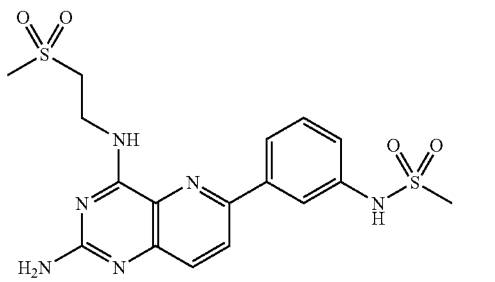 | N-{3-[2-Amino-4-(2-methanesulfonyl-ethylamino)-pyrido[3,2-d]pyrimidin-6-yl]-phenyl}-methanesulfonamide | 437.0 |
| 4 | 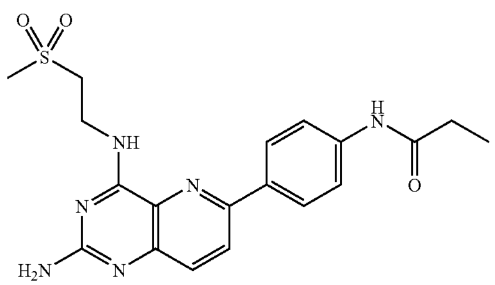 | N-{4-[2-Amino-4-(2-methanesulfonyl-ethylamino)-pyrido[3,2-d]pyrimidin-6-yl]-phenyl}-propionamide | 415.0 |
| 5 | 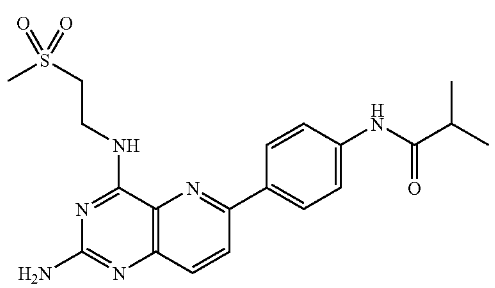 | N-{4-[2-Amino-4-(2-methanesulfonyl-ethylamino)-pyrido[3,2-d]pyrimidin-6-yl]-phenyl}-isobutyramide | 429.1 |
| 6 | 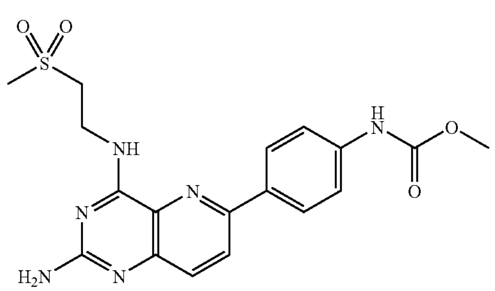 | {4-[2-Amino-4-(2-methanesulfonyl-ethylamino)-pyrido[3,2-d]pyrimidin-6-yl]phenyl}-carbamic acid methyl ester | 417.0 |

TABLE 1-continued

| Example | Structure | Name | Observed Mass M + 1 |
|---|---|---|---|
| 7 | 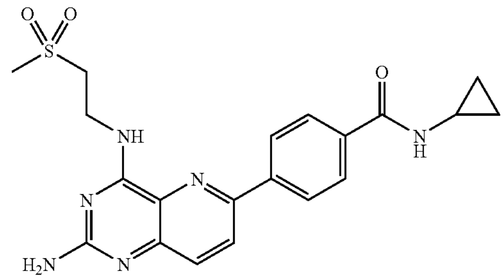 | 4-[2-Amino-4-(2-methanesulfonyl-ethylamino)-pyrido[3,2-d]pyrimidin-6-yl]-N-cyclopropyl-benzamide | 427.0 |

EXAMPLES 8 TO 11

Synthesis of 6-benzamido-N4-(2-methoxy-ethyl)-pyrido[3,2-d]pyrimidin-2-ylamines

Various 6-benzamido-N4-(2-methoxy-ethyl)-pyrido[3,2-d]pyrimidin-2-ylamines were synthesized according to the synthetic sequence outlined in Scheme 2.

Scheme 2

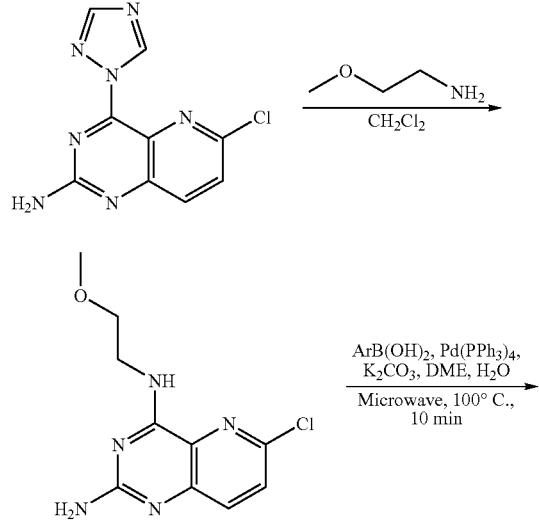

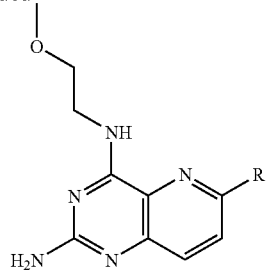

The procedure for the synthesis of 6-chloro-N4-(2-methanesulfonyl-ethyl)-pyrido[3,2-d]pyrimidine-2,4-diamine was repeated, except for the use of 2-methoxyethylamine instead of 2-aminoethylmethylsulfone hydrochloride. The resulting product was characterized by its mass spectrum as follows: MS (m/z) 254.0 [M+H]$^+$.

Then a mixture of 6-chloro-N4-(2-methoxy-ethyl)-pyrido[3,2-d]pyrimidine-2,4-diamine (23 mg), potassium carbonate (27 mg), tetrakis(triphenylphosphine) palladium (8 mg) and a suitable aryl-boronic acid, or a pinacol ester thereof (0.12 mmole) in DME (1.5 mL) and water (1 mL) was heated to 100° C. for 10 minutes under microwave irradiation. Solvents were concentrated in vacuo and the residue was purified by RP HPLC using a C18 column with a gradient of H$_2$O, 0.1% TFA-acetonitrile, to provide the desired product. This procedure provided, with yields ranging from 20% to 65% depending upon the aryl group introduced at the 6-position of the pyrido[3,2-d]pyrimidine ring system, the following pure compounds which were characterized by their mass spectra as indicated in table 2.

TABLE 2

| Example | Structure | Name | Observed Mass M + 1 |
|---|---|---|---|
| 8 | 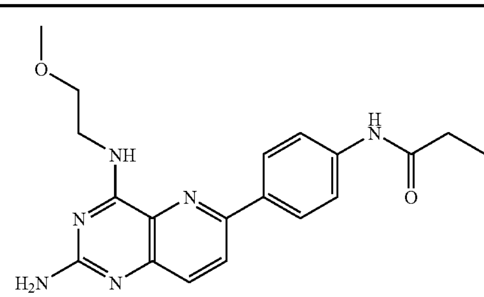 | N-{4-[2-Amino-4-(2-methoxy-ethylamino)-pyrido[3,2-d]pyrimidin-6-yl]-phenyl}-propionamide | 367.1 |

TABLE 2-continued

| Example | Structure | Name | Observed Mass M + 1 |
|---|---|---|---|
| 9 | 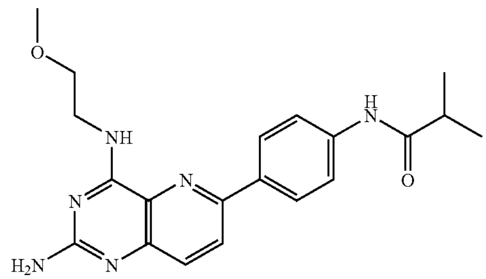 | N-{4-[2-Amino-4-(2-methoxy-ethylamino)-pyrido[3,2-d]pyrimidin-6-yl]-phenyl}-isobutyramide | 381 |
| 10 | 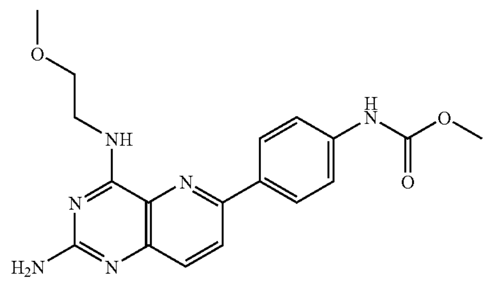 | {4-[2-Amino-4-(2-methoxy-ethylamino)-pyrido[3,2-d]pyrimidin-6-yl]-phenyl}-carbamic acid methyl ester | 369.1 |
| 11 | 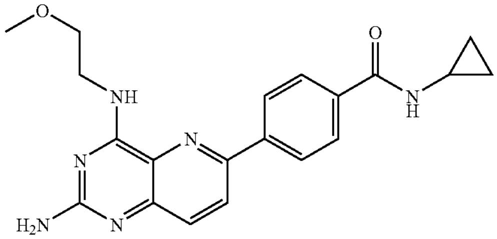 | 4-[2-Amino-4-(2-methoxy-ethylamino)-pyrido[3,2-d]pyrimidin-6-yl]-N-cyclopropyl-benzamide | 379 |

EXAMPLES 12 TO 16

Synthesis of 6-benzamido-4-(1,1-dioxo-1λ$^6$-thiomorpholin-4-yl)-pyrido[3,2-d]pyrimidin-2-ylamines 6-benzamido-4-(1,1-dioxo-1λ$^6$-thiomorpholin-4-yl)-pyrido[3,2-d]pyrimidin-2-yl-amines were synthesized according to the synthetic sequence outlined in Scheme 3.

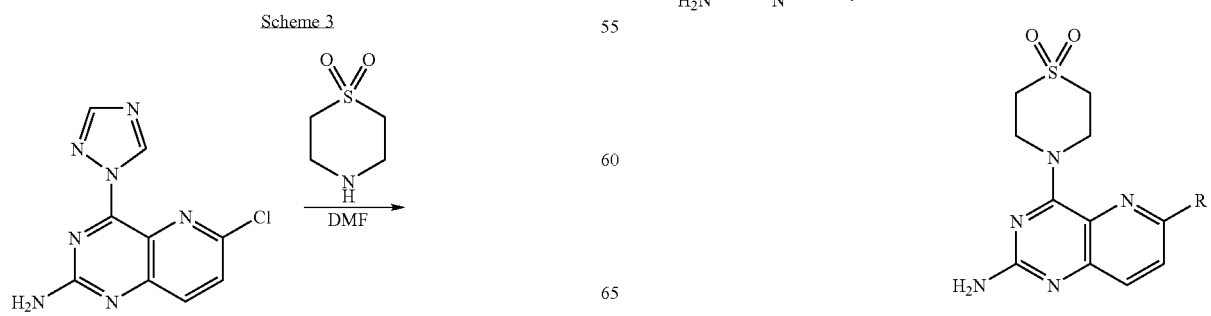

The synthetic procedure of 6-chloro-N4-(2-methanesulfonyl-ethyl)-pyrido[3,2-d]pyrimidine-2,4-diamine was repeated, except for the use of thiomorpholine 1,1-dioxide instead of 2-aminoethylmethylsulfone hydrochloride and DMF as solvent instead of DCM. The desired product, 6-chloro-4-(1,1-dioxo-1λ⁶-thiomorpholin-4-yl)-pyrido[3,2-d]pyrimidin-2-ylamine, was characterized by its mass spectrum as follows: MS (m/z) 314.0 [M+H]⁺.

Then a mixture of 6-chloro-4-(1,1-dioxo-1l6-thiomorpholin-4-yl)-pyrido[3,2-d]pyrimidin-2-ylamine (23 mg), potassium carbonate (27 mg), tetrakis(triphenylphosphine) palladium (8 mg) and a suitable aryl-boronic acid, or a pinacol ester thereof (0.12 mmole) in DME (1.5 mL) and water (1 mL) was heated to 100° C. for 10 minutes under microwave irradiation. Solvents were concentrated in vacuo and the residue was purified by RP HPLC using a C18 column with a gradient of H₂O, 0.1% TFA-acetonitrile, to provide the desired product. This procedure provided, with yields ranging from 20% to 65% depending upon the aryl introduced at the 6-position of the pyrido[3,2-d]pyrimidine ring system, the following pure compounds which were characterized by their mass spectra as indicated in Table 3.

TABLE 3

| Example | Structure | Name | Observed Mass M + 1 |
|---|---|---|---|
| 12 | 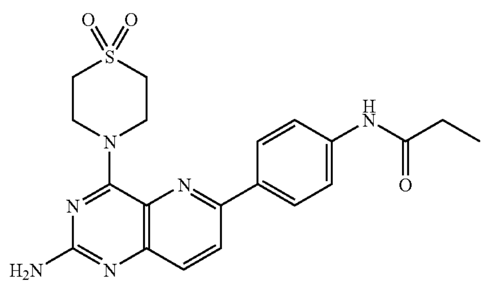 | N-{4-[2-Amino-4-(1,1-dioxo-1λ⁶-thiomorpholin-4-yl)-pyrido[3,2-d]pyrimidin-6-yl]-phenyl}-propionamide | 427 |
| 13 | 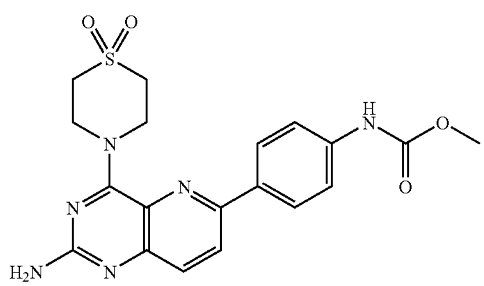 | {4-[2-Amino-4-(1,1-dioxo-1λ⁶-thiomorpholin-4-yl)-pyrido[3,2-d]pyrimidin-6-yl]-phenyl}-carbamic acid methyl ester | 429 |
| 14 | 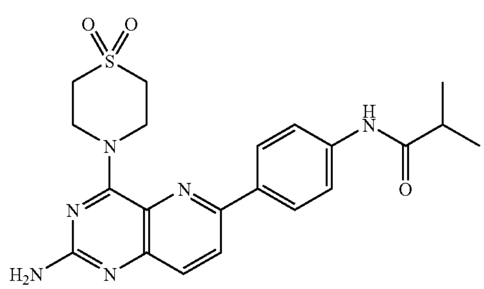 | N-{4-[2-Amino-4-(1,1-dioxo-1λ⁶-thiomorpholin-4-yl)-pyrido[3,2-d]pyrimidin-6-yl]-phenyl}-isobutyramide | 441.1 |
| 15 | 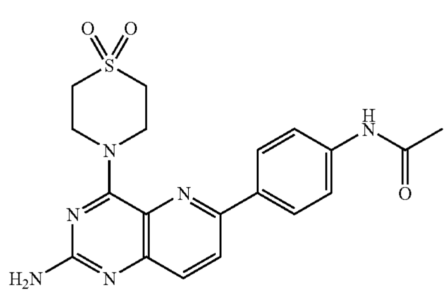 | N-{4-[2-Amino-4-(1,1-dioxo-1λ⁶-thiomorpholin-4-yl)-pyrido[3,2-d]pyrimidin-6-yl]-phenyl}-acetamide | 413 |

TABLE 3-continued

| Example | Structure | Name | Observed Mass M + 1 |
|---|---|---|---|
| 16 | 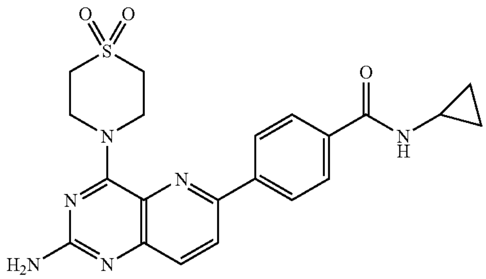 | 4-[2-Amino-4-(1,1-dioxo-1λ⁶-thiomorpholin-4-yl)-pyrido[3,2-d]pyrimidin-6-yl]-N-cyclopropyl-benzamide | 439.1 |

EXAMPLE 17

Synthesis of 4-(2-amino-4-morpholin-4-yl-pyrido[3,2-d]pyrimidin-6-yl)-N-cyclopropyl-benzamide This compound has been synthesized according to the synthetic sequence shown in Scheme 4.

EXAMPLES 18 TO 20

Synthesis of 6-benzamido-4-(2-methoxy-ethoxy)-pyrido[3,2-d]pyrimidin-2-ylamines

Various 6-benzamido-4-(2-methoxy-ethoxy)-pyrido[3,2-d]pyrimidin-2-ylamines were synthesized according to the synthetic sequence outlined in Scheme 5.

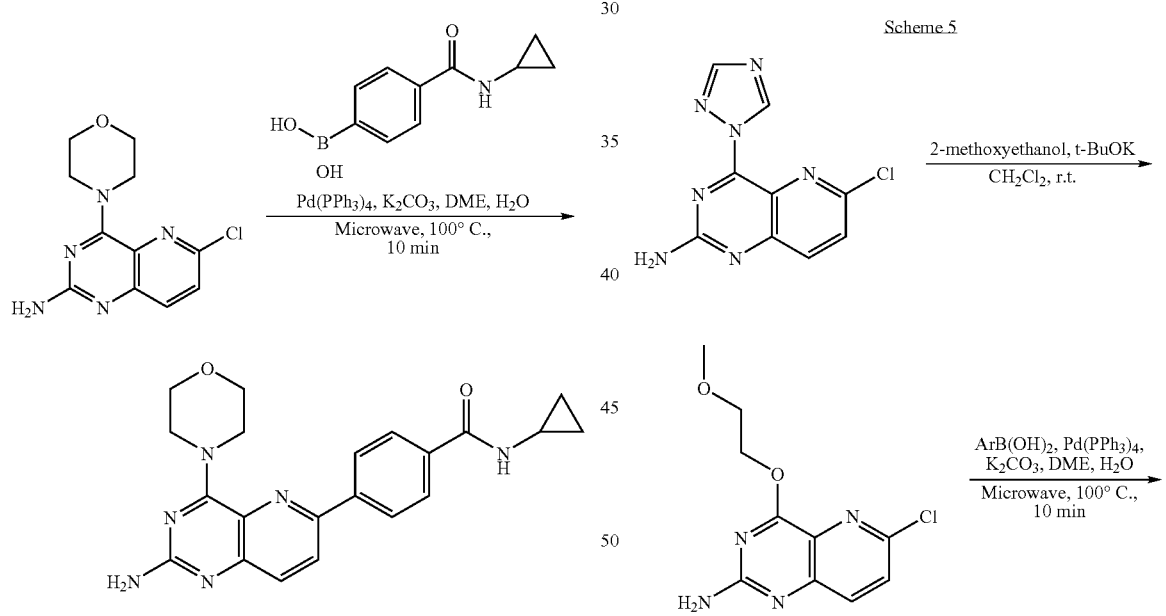

A mixture of 6-chloro-4-morpholin-4-yl-pyrido[3,2-d]pyrimidin-2-ylamine (26 mg), potassium carbonate (28 mg), tetrakis(triphenylphosphine) palladium (10 mg) and 4-(N-cyclopropylaminocarbonyl)phenylboronic acid (21 mg) in DME (2 mL) and water (1 mL) was heated to 100° C. for 10 minutes by microwave. Solvents were concentrated in vacuo and the residue was purified by RP HPLC using a C18 column with a gradient of $H_2O$, 0.1% TFA-acetonitrile, to provide the desired product (6.8 mg, yield: 18%) which was characterized by its mass spectrum as follows: MS (m/z) 391.1 $[M+H]^+$.

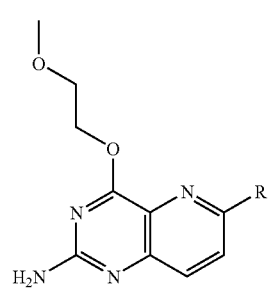

Potassium tert-butoxide (4 mL; 1M in THF) was added to a suspension mixture of 6-chloro-4-[1,2,4]triazol-1-yl-pyrido[3,2-d]pyrimidin-2-ylamine (1 g) and 2-methoxyethanol (0.32 mL) in DCM (50 mL). After stirring at room temperature for 10 minutes, the mixture was diluted with DCM (100 mL) and washed with brine. The organic layer was dried over $Na_2SO_4$ and concentrated to afford 6-chloro-4-(2-methoxy-ethoxy)-pyrido[3,2-d]pyrimidin-2-ylamine as a beige solid (0.91 g, yield: 90%) which was characterized by its mass spectrum as follows: MS (m/z) 225.0 $[M+H]^+$.

Then a mixture of 6-chloro-4-(2-methoxy-ethoxy)-pyrido[3,2-d]pyrimidin-2-ylamine (15 mg), potassium carbonate (16 mg), tetrakis(triphenylphosphine) palladium (10 mg) and a suitable aryl-boronic acid, or a pinacol ester thereof, (0.08 mmole) in DME (1 mL) and water (0.5 mL) was heated to 100° C. for 10 minutes by microwave. Solvents were concentrated in vacuo and the residue was purified by RP HPLC using a C18 column with a gradient of $H_2O$, 0.1% TFA-acetonitrile, to provide the desired product. This procedure provided, with yields ranging from 30% to 70% depending upon the aryl group introduced at the 6-position of the pyrido[3,2-d]pyrimidine ring, the following pure compounds which were characterized by their mass spectrum MS as indicated in Table 4 below.

EXAMPLE 21

Synthesis of N-{4-[2-amino-4-(2-fluoro-ethoxy)-pyrido[3,2-d]pyrimidin-6-yl]-phenyl}-isobutyramide This compound was synthesized according to the synthetic sequence outlined in Scheme 6.

Scheme 6

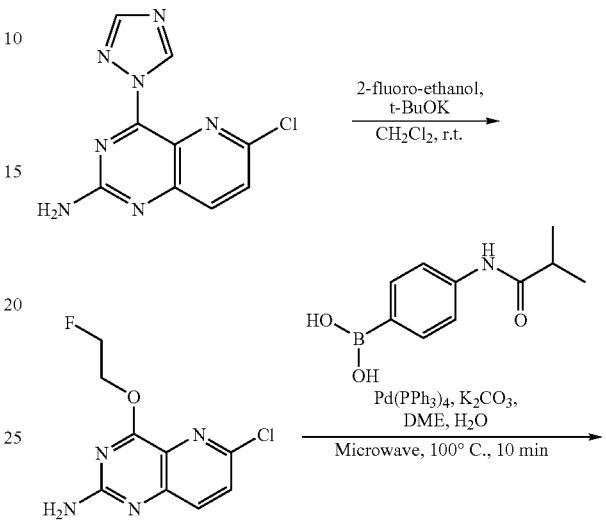

TABLE 4

| Example | Structure | Name | Observed Mass M + 1 |
|---|---|---|---|
| 18 | 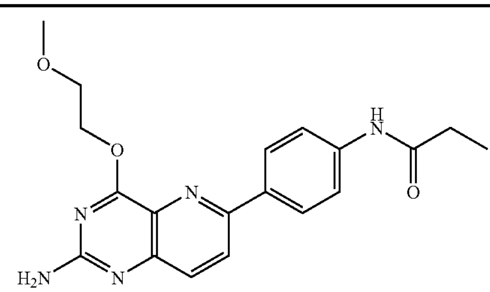 | N-{4-[2-Amino-4-(2-methoxy-ethoxy)-pyrido[3,2-d]pyrimidin-6-yl]-phenyl}-propionamide | 368.1 |
| 19 | 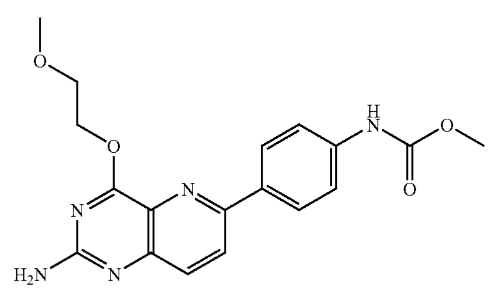 | {4-[2-Amino-4-(2-methoxy-ethoxy)-pyrido[3,2-d]pyrimidin-6-yl]-phenyl}-carbamic acid methyl ester | 370.0 |
| 20 | 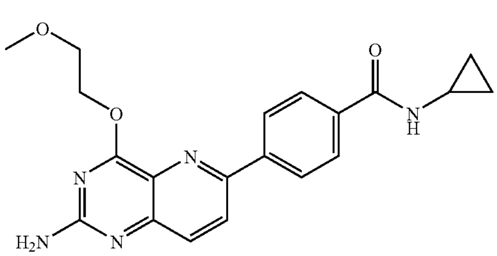 | 4-[2-Amino-4-(2-methoxy-ethoxy)-pyrido[3,2-d]pyrimidin-6-yl]-N-cyclopropyl-benzamide | 380.1 |

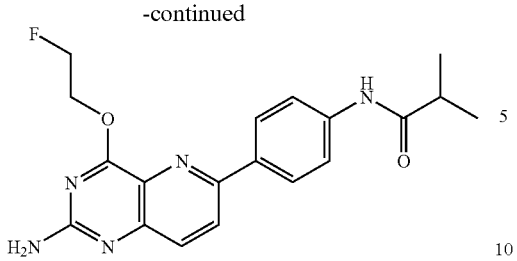

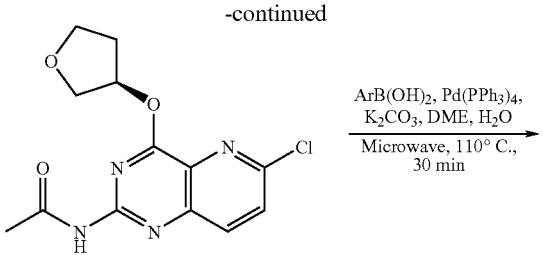

Potassium tert-butoxide (2.8 mL; 1M in THF) was added to a suspension of 6-chloro-4-[1,2,4]triazol-1-yl-pyrido[3,2-d]pyrimidin-2-ylamine (0.7 g) and 2-fluoroethanol (0.83 mL) in DCM (100 mL). After stirring at room temperature for 10 minutes, the mixture was diluted with DCM (100 mL) and washed with brine. The organic layer was dried over $Na_2SO_4$ and concentrated to afford 6-chloro-4-(2-fluoro-ethoxy)-pyrido[3,2-d]pyrimidin-2-ylamine as a yellow solid (0.3 g, yield: 44%) was characterized by its mass spectrum as follows: MS (m/z) 243.1 [M+H]$^+$.

Then a mixture of 6-chloro-4-(2-fluoro-ethoxy)-pyrido[3,2-d]pyrimidin-2-ylamine (15 mg), potassium carbonate (16 mg), tetrakis(triphenylphosphine) palladium (10 mg) and 4-isobutyramidophenylboronic acid (0.08 mmol) in DME (2 mL) and water (1 mL) was heated to 100° C. for 10 minutes by microwave. Solvents were concentrated in vacuo and the residue was purified by RP HPLC a C18 column with a gradient of $H_2O$, 0.1% TFA-acetonitrile, to provide the desired product (4.4 mg, yield: 23%) which was characterized by its mass spectrum as follows: MS (m/z) 370 [M+H]$^+$.

EXAMPLES 22 TO 28

Synthesis of 6-benzamido-4-(tetrahydro-furan-3-yloxy)-pyrido[3,2-d]pyrimidin-2-ylamines Various 6-benzamido-4-(tetrahydro-furan-3-yloxy)-pyrido[3,2-d]pyrimidin-2-ylamines were synthesized according to the general synthetic sequence outlined in Scheme 7.

Scheme 7

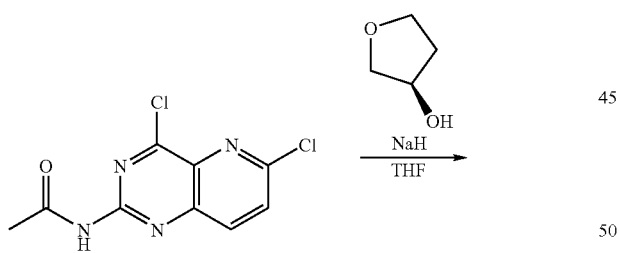

(R)-(−)-3-hydroxy-tetrahydrofuran (0.62 mL) was added to a suspension of NaH (0.31 g, 7.7 mmol) in THF (15 mL). After stirring for 1 hour, the resulting mixture was added to a suspension of N-(4,6-dichloro-pyrido[3,2-d]pyrimidin-2-yl)-acetamide (0.9 g, 3.5 mmol) in THF (15 mL). The mixture was stirred at room temperature for 20 minutes, then diluted with EtOAC (100 mL) and washed with brine. The organic layer was dried over $Na_2SO_4$ and concentrated to afford 6-chloro-4-(tetrahydro-furan-3-yloxy)-pyrido[3,2-d]pyrimidin-2-ylamine as a yellow solid (0.55 g, yield: 51%) which was characterized by its mass spectrum as follows: MS (m/z) 309.1 [M+H]$^+$.

Then a mixture of N-[6-chloro-4-(tetrahydro-furan-3-yloxy)-pyrido[3,2-d]pyrimidin-2-yl]-acetamide (15 mg), potassium carbonate (16 mg), tetrakis(triphenylphosphine) palladium (10 mg) and the corresponding boronic acid or pinacol ester (0.08 mmole) in DME (1 mL) and water (0.5 mL) was heated to 110° C. for 30 minutes by microwave. Solvents were concentrated in vacuo and the residue was purified by RP HPLC using a C18 column with a gradient of $H_2O$, 0.1% TFA-acetonitrile, to provide the desired product. This procedure provided, with yields ranging from 10% to 60% depending upon the aryl introduced at the 6-position of the pyrido[3,2-d]pyrimidine ring, the following pure compounds which were characterized by their mass spectrum MS as indicated in table 5.

TABLE 5

| Example | Structure | Name | Observed Mass M + 1 |
|---|---|---|---|
| 22 | 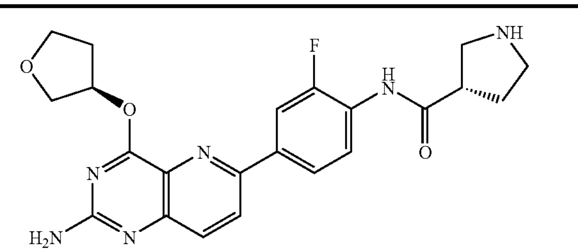 | Pyrrolidine-3-carboxylic acid {4-[2-amino-4-(tetrahydro-furan-3-yloxy)-pyrido[3,2-d]pyrimidin-6-yl]-2-fluoro-phenyl}-amide | 439.1 |

TABLE 5-continued

| Example | Structure | Name | Observed Mass M + 1 |
|---|---|---|---|
| 23 | 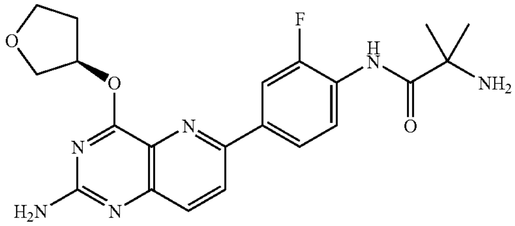 | 2-Amino-N-{4-[2-amino-4-(tetrahydro-furan-3-yloxy)-pyrido[3,2-d]pyrimidin-6-yl]-2-fluoro-phenyl}-2-methyl-propionamide | 427.1 |
| 24 | 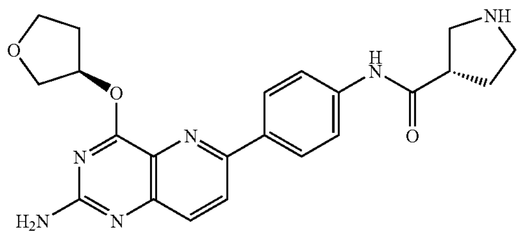 | Pyrrolidine-3-carboxylic acid {4-[2-amino-4-(tetrahydro-furan-3-yloxy)-pyrido[3,2-d]pyrimidin-6-yl]-phenyl}-amide | 421.1 |
| 25 | 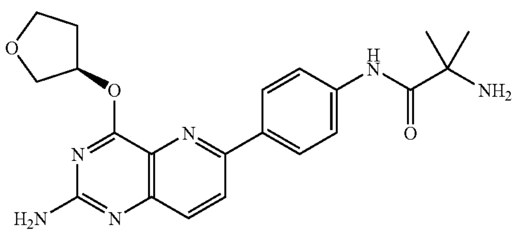 | 2-Amino-N-{4-[2-amino-4-(tetrahydro-furan-3-yloxy)-pyrido[3,2-d]pyrimidin-6-yl]-phenyl}-2-methyl-propionamide | 409.1 |
| 26 | 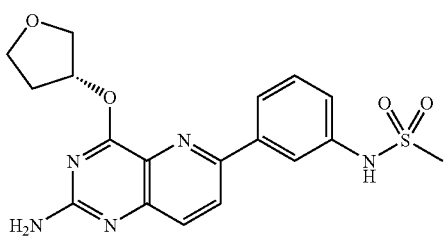 | N-{3-[2-Amino-4-(tetrahydro-furan-3-yloxy)-pyrido[3,2-d]pyrimidin-6-yl]-phenyl}-methanesulfonamide | 402.0 |
| 27 | 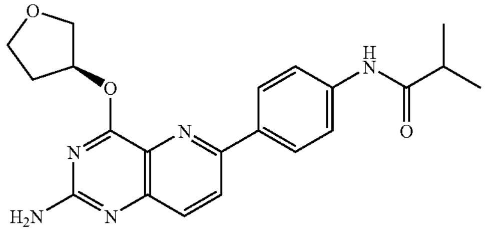 | N-{4-[2-Amino-4-(tetrahydro-furan-3-yloxy)-pyrido[3,2-d]pyrimidin-6-yl]-phenyl}-isobutyramide | 394.1 |
| 28 | 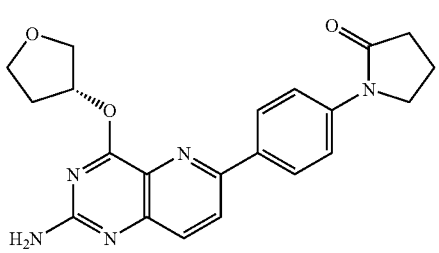 | 1-{4-[2-Amino-4-(tetrahydro-furan-3-yloxy)-pyrido[3,2-d]pyrimidin-6-yl]-phenyl}-pyrrolidin-2-one | 392.1 |

45
EXAMPLE 29

Synthesis of N-[4-(2-amino-4-isopropoxy-pyrido[3,2-d]pyrimidin-6-yl)-phenyl]-isobutyramide This compound was synthesized according to the synthetic sequence outlined in Scheme 8.

Briefly, the procedure of N-{4-[2-amino-4-(tetrahydro-furan-3-yloxy)-pyrido[3,2-d]pyrimidin-6-yl]-phenyl}-isobutyramide was repeated, except for the use of N-(6-chloro-4-isopropoxy-pyrido[3,2-d]pyrimidin-2-yl)-acetamide instead of N-[6-chloro-4-(tetrahydro-furan-3-yloxy)-pyrido[3,2-d]pyrimidin-2-yl]-acetamide. The resulting product was characterized by its mass spectrum as follows: MS (m/z) 366.1 [M+H]$^+$.

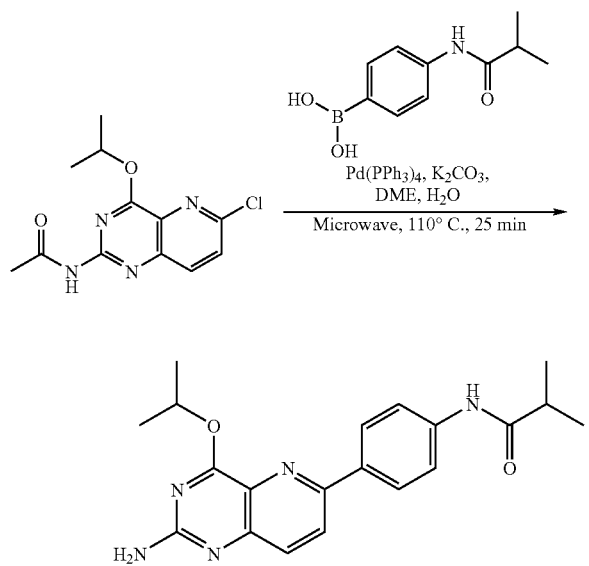

Scheme 8

46
EXAMPLES 30 TO 46

Synthesis of 6-benzamido-4-ethoxy-pyrido[3,2-d]pyrimidin-2-ylamines

Various 6-benzamido-4-ethoxy-pyrido[3,2-d]pyrimidin-2-ylamines were synthesized according to the synthetic sequence outlined in Scheme 9.

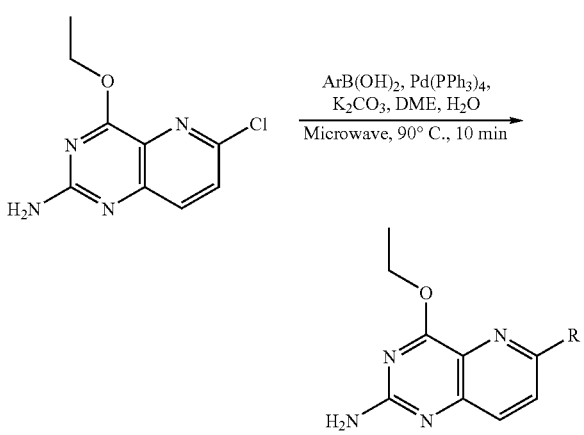

Scheme 9

A mixture of 6-chloro-4-ethoxy-pyrido[3,2-d]pyrimidin-2-ylamine (15 mg, 0.06 mmol), potassium carbonate (16 mg, 0.12 mmol), tetrakis(triphenylphosphine) palladium (10 mg) and the corresponding boronic acid or pinacol ester (0.08 mmol) in DME (1.5 mL) and water (0.5 mL) was heated to 90° C. for 10 minutes by microwave. Solvents were concentrated in vacuo and the residue was purified by RP HPLC using a C18 column with a gradient of H$_2$O, 0.1% TFA-acetonitrile, to provide the desired product. This procedure provided, with yields ranging from 10% to 60% depending upon the aryl or heteroaryl group introduced at the 6-position of the pyrido[3,2-d]pyrimidine ring, the following pure final compounds which were characterized by their mass spectrum MS as indicated in the following table 6.

TABLE 6

| Ex. | Structure | Name | Obs. Mass M + 1 |
|---|---|---|---|
| 30 | 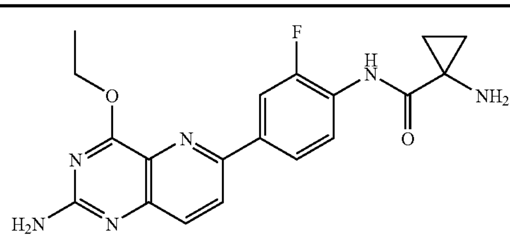 | 1-Amino-cyclopropanecarboxylic acid [4-(2-amino-4-ethoxy-pyrido[3,2-d]pyrimidin-6-yl)-2-fluoro-phenyl]-amide | 383.1 |
| 31 | 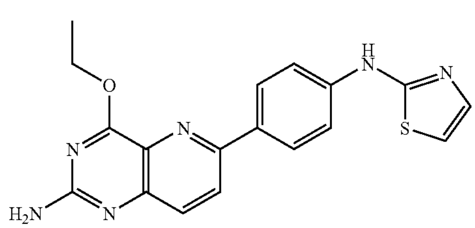 | 4-Ethoxy-6-[4-(thiazol-2-ylamino)-phenyl-pyrido[3,2-d]pyrimidin-2-ylamine | 365.0 |

TABLE 6-continued

| Ex. | Structure | Name | Obs. Mass M + 1 |
|---|---|---|---|
| 32 | 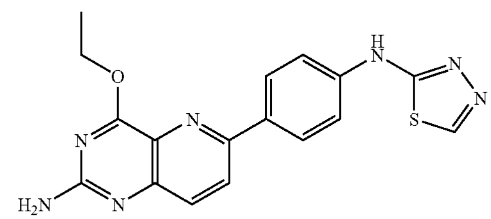 | 4-Ethoxy-6-[4-([1,3,4]thiadiazol-2-ylamino)-phenyl]-pyrido[3,2-d]pyrimidin-2-ylamine | 366.0 |
| 33 | 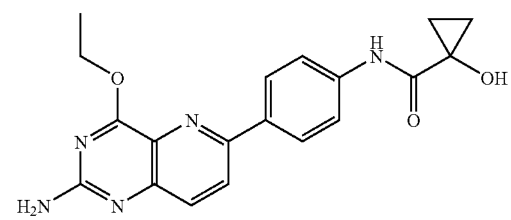 | 1-Hydroxy-cyclopropanecarboxylic acid [4-(2-amino-4-ethoxy-pyrido[3,2-d]pyrimidin-6-yl)-phenyl]-amide | 366.1 |
| 34 | 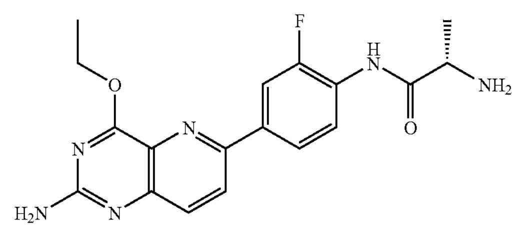 | 2-Amino-N-[4-(2-amino-4-ethoxy-pyrido[3,2-d]pyrimidin-6-yl)-2-fluoro-phenyl]-propanamide | 371.0 |
| 35 | 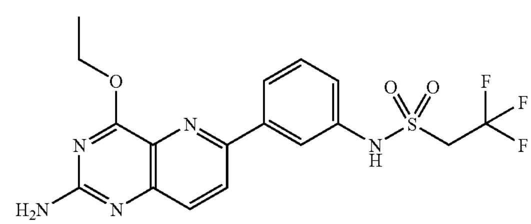 | 2,2,2-Trifluoro-ethanesulfonic acid [3-(2-amino-4-ethoxy-pyrido[3,2-d]pyrimidin-6-yl)-phenyl]-amide | 428.0 |
| 36 | 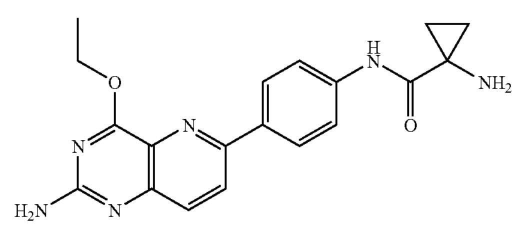 | 1-Amino-cyclopropanecarboxylic acid [4-(2-amino-4-ethoxy-pyrido[3,2-d]pyrimidin-6-yl)-phenyl]-amide | 365.1 |
| 37 | 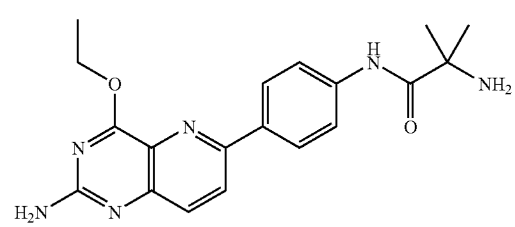 | 2-Amino-N-[4-(2-amino-4-ethoxy-pyrido[3,2-d]pyrimidin-6-yl)-phenyl]-2-methyl-propionamide | 367.1 |

TABLE 6-continued

| Ex. | Structure | Name | Obs. Mass M + 1 |
|---|---|---|---|
| 38 | 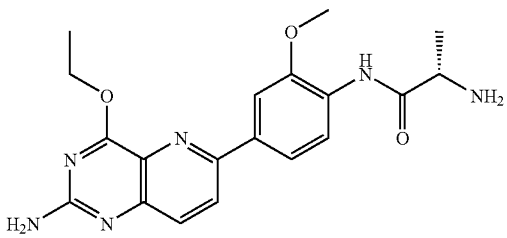 | 2-Amino-N-[4-(2-amino-4-ethoxy-pyrido[3,2-d]pyrimidin-6-yl)-2-methoxy-phenyl]-propionamide | 383.1 |
| 39 | 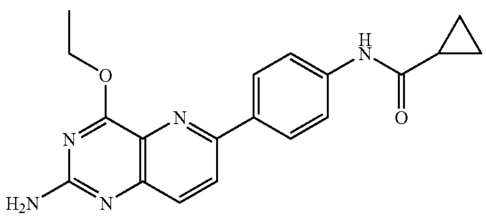 | Cyclopropanecarboxylic acid [4-(2-amino-4-ethoxy-pyrido[3,2-d]pyrimidin-6-yl)-phenyl]-amide | 350.1 |
| 40 | 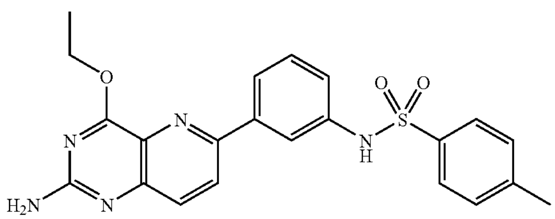 | N-]3-(2-Amino-4-ethoxy-pyrido[3,2-d]pyrimidin-6-yl)-phenyl]-4-methyl-benzenesulfonamide | 436.1 |
| 41 | 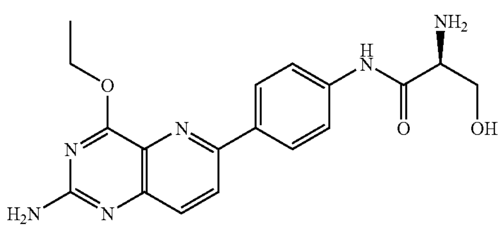 | 2-Amino-N-[4-(2-amino-4-ethoxy-pyrido[3,2-d]pyrimidin-6-yl)-phenyl]-3-hydroxy-propionamide | 369.1 |
| 42 | 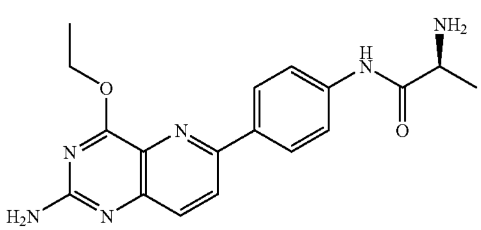 | 2-Amino-N-[4-(2-amino-4-ethoxy-pyrido[3,2-d]pyrimidin-6-yl)-phenyl]-propionamide | 353.2 |
| 43 | 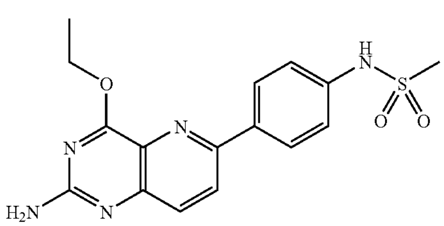 | N-[4-(2-Amino-4-ethoxy-pyrido[3,2-d]pyrimidin-6-yl)-phenyl]-methanesulfonamide | 360.1 |

TABLE 6-continued

| Ex. | Structure | Name | Obs. Mass M + 1 |
|---|---|---|---|
| 44 | 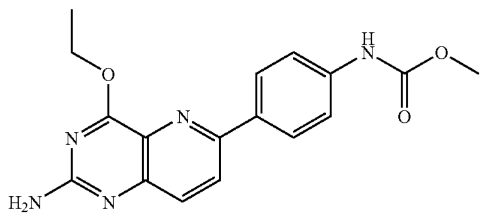 | [4-(2-Amino-4-ethoxy-pyrido[3,2-d]pyrimidin-6-yl)-phenyl]-carbamic acid methyl ester | 340.1 |
| 45 | 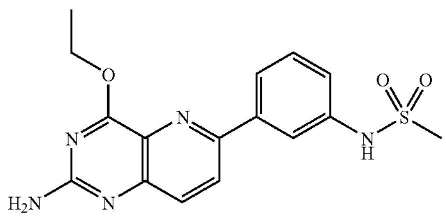 | N-[3-(2-Amino-4-ethoxy-pyrido[3,2-d]pyrimidin-6-yl)-phenyl]-methanesulfonamide | 360.1 |
| 46 | 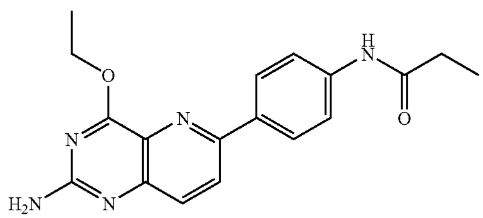 | N-[4-(2-Amino-4-ethoxy-pyrido[3,2-d]pyrimidin-6-yl)-phenyl]-propionamide | 338.1 |

EXAMPLE 47

Synthesis of 6-(5-amino-thiazol-2-yl)-4-ethoxy-pyrido[3,2-d]pyrimidin-2-ylamine

This compound was synthesized according to the synthetic sequence outlined in Scheme 10.

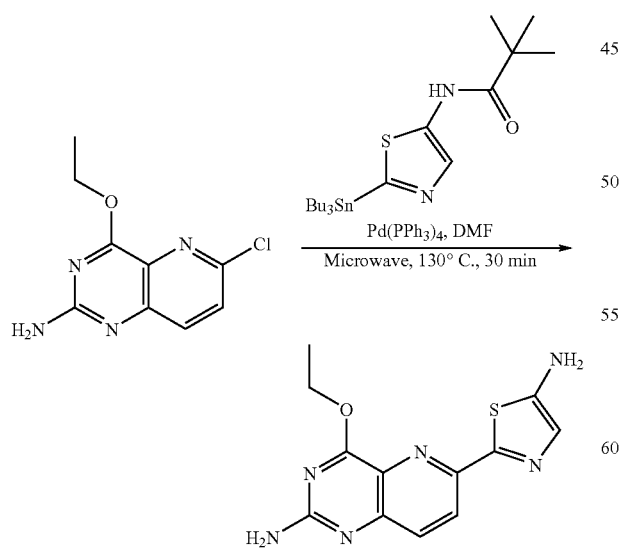

Scheme 10

A mixture of 6-chloro-4-ethoxy-pyrido[3,2-d]pyrimidin-2-ylamine (22 mg), tetrakis(triphenylphosphine) palladium (10 mg) and 2,2-Dimethyl-N-(2-tributylstannanyl-thiazol-5-yl)-propionamide (49 mg) in DMF (2 mL) was heated to 130° C. for 30 minutes by microwave. Solvents were concentrated in vacuo and the residue was purified by RP HPLC using a C18 column with a gradient of $H_2O$, 0.1% TFA-acetonitrile, to provide the desired product (5 mg, yield: 10%) which was characterized by its mass spectrum as follows: MS (m/z) 289.0 $[M+H]^+$.

EXAMPLES 48 TO 54

Synthesis of sulfonic acid [3-(2-amino-4-ethoxy-pyrido[3,2-d]pyri-midin-6-yl)-phenyl]-amides Various sulfonic acid [3-(2-amino-4-ethoxy-pyrido[3,2-d]pyrimidin-6-yl)-phenyl]-amides were synthesized according to the general synthetic sequence outlined in Scheme 11.

Scheme 11

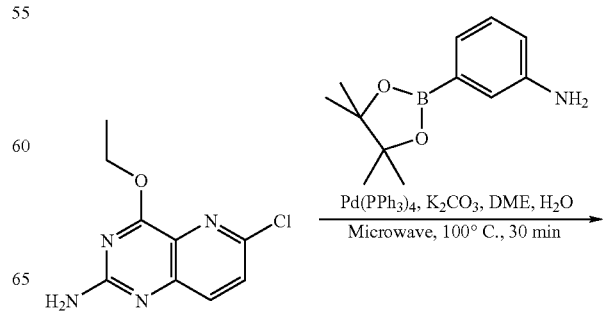

-continued

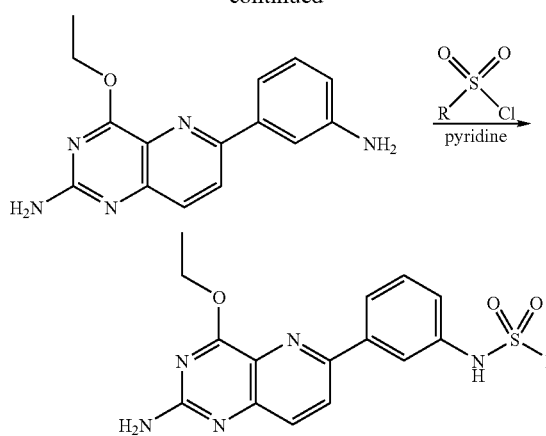

The procedure of cyclopropanecarboxylic acid [4-(2-amino-4-ethoxy-pyrido[3,2-d]pyrimidin-6-yl)-phenyl]-amide (example 39) was repeated, except for the use of 3-(4,4,5,5-tetramethyl-[1,3,2]dioxaborolan-2-yl)-phenylamine instead of 4-(N-cyclopropyl-aminocarbonyl)phenylboronic acid. The desired product, 6-(3-amino-phenyl)-4-ethoxy-pyrido[3,2-d]pyrimidin-2-ylamine, was characterized by its mass spectrum as follows: MS (m/z) 282.0 [M+H]$^+$.

To a solution of 6-(3-amino-phenyl)-4-ethoxy-pyrido[3,2-d]pyrimidin-2-ylamine (28 mg) in pyridine (1 mL) was added the corresponding sulfonyl chloride (0.11 mmole) at 0° C. The mixture was stirred at 0° C. until reaction was complete, as judged by LC/MS. Solvent was removed and the residue was purified by RP HPLC using a C18 column with a gradient of H$_2$O, 0.05% TFA-acetonitrile, to provide the desired product. This procedure provided, with yields ranging from 30% to 70% depending upon the sulfonyl group introduced at the 3-amino-phenyl position of the pyrido[3,2-d]pyrimidine ring, the following pure compounds which were characterized by their mass spectrum MS as indicated in table 7.

TABLE 7

| Ex. | Structure | Name | Obs. Mass M + 1 |
|---|---|---|---|
| 48 | 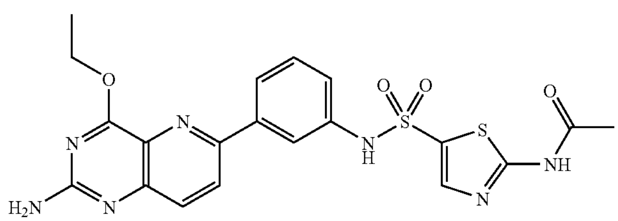 | N-{5-[3-(2-Amino-4-ethoxy-pyrido[3,2-d]pyrimidin-6-yl)-phenylsulfamoyl]-thiazol-2-yl}-acetamide | 486.0 |
| 49 | 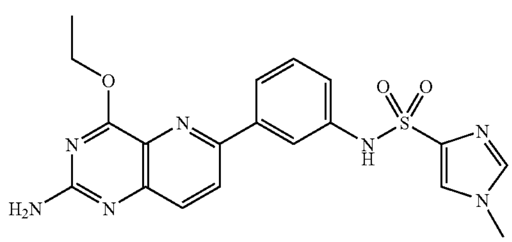 | 1-Methyl-1H-imidazole-4-sulfonic acid [3-(2-amino-4-ethoxy-pyrido[3,2-d]pyrimidin-6-yl)-phenyl]-amide | 426.0 |
| 50 | 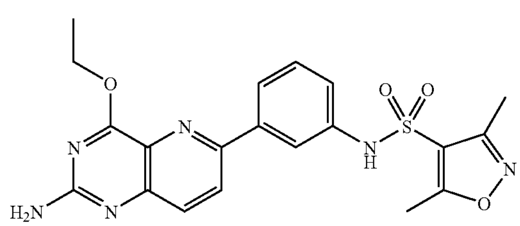 | 3,5-Dimethyl-isoxazole-4-sulfonic acid [3-(2-amino-4-ethoxy-pyrido[3,2-d]pyrimidin-6-yl)-phenyl]-amide | 441.1 |
| 51 | 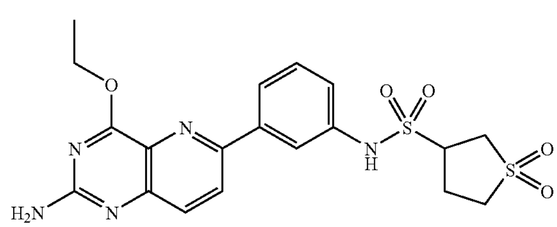 | 1,1-Dioxo-tetrahydro-1?$^6$-thiophene-3-sulfonic acid [3-(2-amino-4-ethoxy-pyrido[3,2-d]pyrimidin-6-yl)-phenyl]-amide | 434.0 |

TABLE 7-continued

| Ex. | Structure | Name | Obs. Mass M + 1 |
|---|---|---|---|
| 52 | 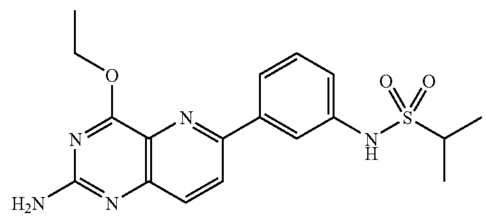 | Propane-2-sulfonic acid[3-(2-amino-4-ethoxy-pyrido[3,2-d]pyrimidin-6-yl)-phenyl]-amide | 388.0 |
| 53 | 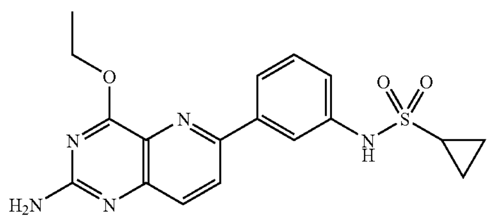 | Cyclopropanesulfonic acid[3-(2-amino-4-ethoxy-pyrido[3,2-d]pyrimidin-6-yl)-phenyl]-amide | 358.8 |
| 54 | 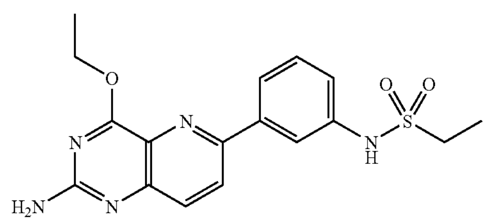 | Ethanesulfonic acid [3-(2-amino-4-ethoxy-pyrido[3,2-d]pyrimidin-6-yl)-phenyl]-amide | 374.0 |

EXAMPLE 55

Synthesis of ethanesulfonic acid [4-(2-amino-4-ethoxy-pyrido[3,2-d]pyrimidin-6-yl)-phenyl]-amide This compound was synthesized according to the synthetic scheme outlined in Scheme 12.

Scheme 12

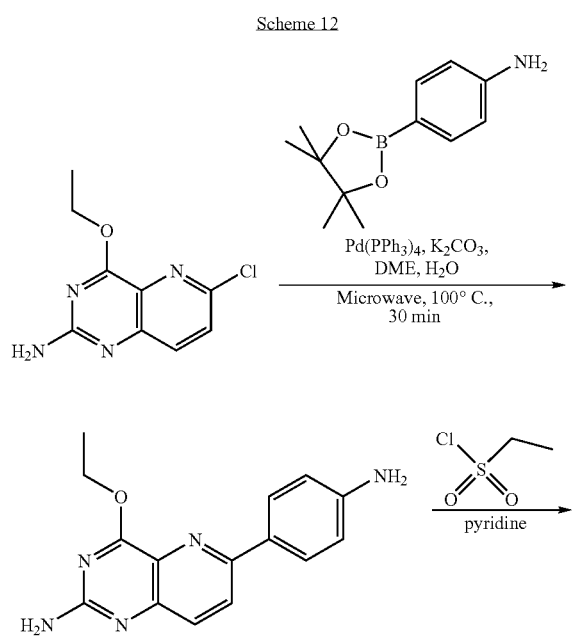

-continued

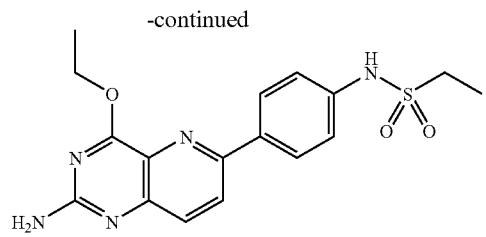

The procedure of cyclopropanecarboxylic acid [4-(2-amino-4-ethoxy-pyrido[3,2-d]pyrimidin-6-yl)-phenyl]-amide was repeated, except for the use of 4-(4,4,5,5-Tetramethyl-[1,3,2]dioxaborolan-2-yl)-phenylamine instead of 4-(N-cyclopropylamino-carbonyl)phenylboronic acid. The resulting product, 6-(4-amino-phenyl)-4-ethoxy-pyrido[3,2-d]pyrimidin-2-ylamine, was characterized by its mass spectrum as follows: MS (m/z) 282.0 [M+H]$^+$.

Then the procedure of propane-2-sulfonic acid [3-(2-amino-4-ethoxy-pyrido[3,2-d]pyrimidin-6-yl)-phenyl]-amide is repeated, except for the use of ethanesulfonyl chloride instead of isopropylsulfonyl chloride and 6-(4-amino-phenyl)-4-ethoxy-pyrido[3,2-d]pyrimidin-2-ylamine instead of 6-(3-amino-phenyl)-4-ethoxy-pyrido[3,2-d]pyrimidin-2-ylamine. The resulting product was characterized by its mass spectrum as follows: MS (m/z) 374.0 [M+H]$^+$.

EXAMPLES 56 TO 63

Synthesis of 6-benzamido-4-ethoxy-pyrido[3,2-d]pyrimidin-2-yl-amines

Various 6-benzamido-4-ethoxy-pyrido[3,2-d]pyrimidin-2-ylamines were synthesized according to the general procedure outlined in Scheme 13.

Scheme 13

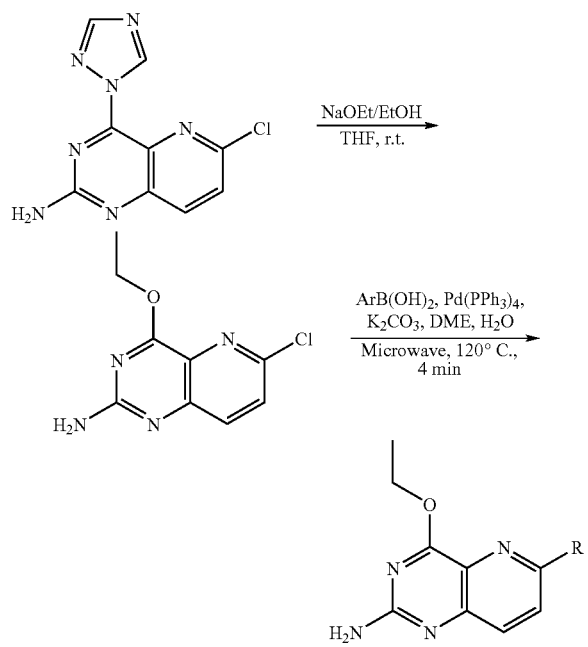

Sodium ethoxide (2.2 mL; 21 wt % in ethanol) was added to a suspension of 6-chloro-4-[1,2,4]triazol-1-yl-pyrido[3,2-d]pyrimidin-2-ylamine (1 g) in THF (50 mL). After stirring at room temperature for 30 minutes, THF was removed in vacuo and the residue was diluted with ethyl acetate (100 mL) and washed with brine. The organic layer was dried over $Na_2SO_4$ and concentrated to afford 6-chloro-4-ethoxy-pyrido[3,2-d]pyrimidin-2-ylamine as a beige solid (0.71 g, yield: 79%) which was characterized by its mass spectrum as follows: MS (m/z) 225.0 $[M+H]^+$.

A mixture of 6-Chloro-4-ethoxy-pyrido[3,2-d]pyrimidin-2-ylamine (20 mg, 0.08 mmol), potassium carbonate (0.17 mmole), tetrakis(triphenylphosphine) palladium (10 mg) and a suitable aryl-boronic acid, or a pinacol ester thereof, (0.1 mmole) in DME (1 mL) and water (0.5 mL) was heated at 120° C. for 4 minutes by microwave. Solvents were concentrated in vacuo and the residue was purified by RP HPLC, using a C18 column with a gradient of $H_2O$, 0.1% TFA-acetonitrile, to provide the desired product. This procedure provided, with yields ranging from 30% to 70% depending upon the aryl group introduced at the 6-position of the pyrido[3,2-d]pyrimidine ring, the following pure compounds, which were characterized by their mass spectrum MS as indicated in the following table 8.

TABLE 8

| Example | Structure | Name | Observed Mass M + 1 |
|---|---|---|---|
| 56 | 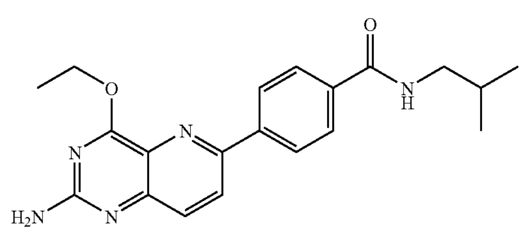 | 4-(2-Amino-4-ethoxy-pyrido[3,2-d]pyrimidin-6-yl)-N-isobutyl-benzamide | 366.1 |
| 57 | 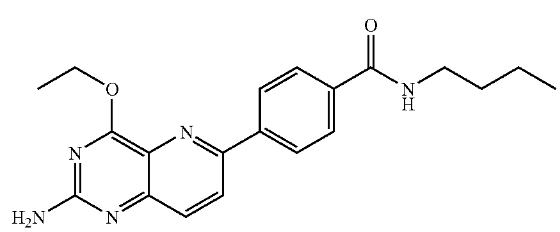 | 4-(2-Amino-4-ethoxy-pyrido[3,2-d]pyrimidin-6-yl)-N-butyl-benzamide | 366.1 |
| 58 | 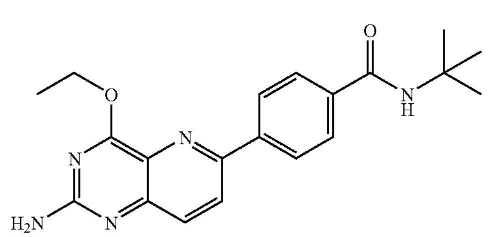 | 4-(2-Amino-4-ethoxy-pyrido[3,2-d]pyrimidin-6-yl)-N-tert-butyl-benzamide | 366.3 |

TABLE 8-continued

| Example | Structure | Name | Observed Mass M + 1 |
|---|---|---|---|
| 59 | 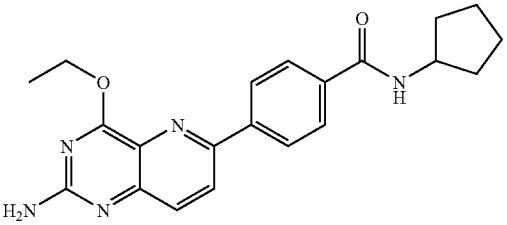 | 4-(2-Amino-4-ethoxy-pyrido[3,2-d]pyrimidin-6-yl)-N-cyclopentyl-benzamide | 378.3 |
| 60 | 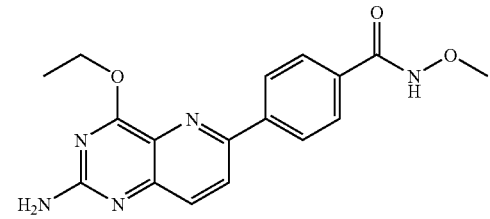 | 4-(2-Amino-4-ethoxy-pyrido[3,2-d]pyrimidin-6-yl)-N-methoxy-benzamide | 340.3 |
| 61 | 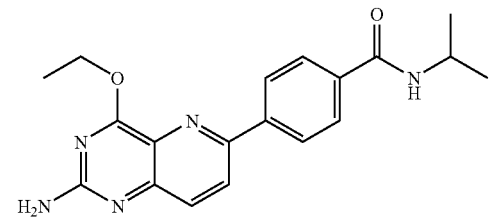 | 4-(2-Amino-4-ethoxy-pyrido[3,2-d]pyrimidin-6-yl)-N-isopropyl-benzamide | 352.3 |
| 62 | 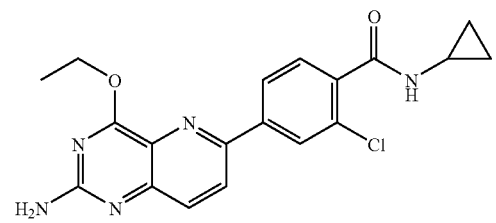 | 4-(2-Amino-4-ethoxy-pyrido[3,2-d]pyrimidin-6-yl)-2-chloro-N-cyclopropyl-benzamide | 384.1 |
| 63 | 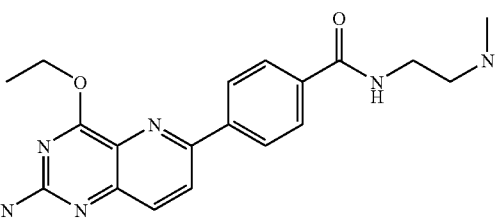 | 4-(2-Amino-4-ethoxy-pyrido[3,2-d]pyrimidin-6-yl)-N-(2-dimethylamino-ethyl)-benzamide | 381.0 |

EXAMPLES 64 TO 74

Synthesis of 6-benzamido-4-(2-propoxy)-pyrido[3,2-d]pyrimidin-2-ylamines

Various 6-benzamido-4-(2-propoxy)-pyrido[3,2-d]pyrimidin-2-ylamines were synthesized according to the general synthetic sequence outlined in Scheme 14.

Scheme 14

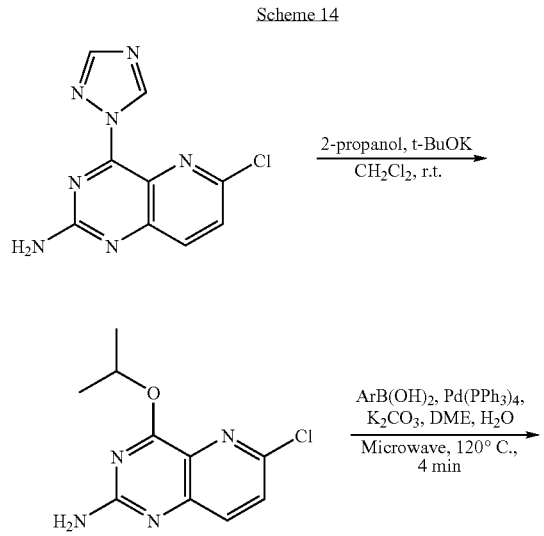

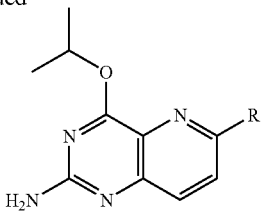

Potassium tert-butoxide (4.0 mL; 1M in THF) was added to a suspension of 6-chloro-4-[1,2,4]triazol-1-yl-pyrido[3,2-d]pyrimidin-2-ylamine (1.0 g) and 2-propanol (0.313 mL) in DCM (50 mL). After stirring at room temperature for 30 minutes, the mixture was diluted with DCM (100 mL) and washed with brine. The organic layer was dried over $Na_2SO_4$ and concentrated to afford 6-chloro-4-(2-propoxy)-pyrido[3,2-d]pyrimidin-2-ylamine as a yellow solid (0.65 g, yield: 67%) which was characterized by its mass spectrum as follows: MS (m/z) 239.1 $[M+H]^+$.

Then a mixture of 6-chloro-4-(2-propoxy-pyrido[3,2-d]pyrimidin-2-ylamine (21.2 mg), potassium carbonate (0.17 mmol), tetrakis(triphenylphosphine) palladium (10 mg) and the corresponding boronic acid or pinacol ester (0.1 mmol) in DME (1 mL) and water (0.5 mL) was heated at 120° C. for 4 minutes by microwave. Solvents were concentrated in vacuo and the residue was purified by RP HPLC using a C18 column with a gradient of $H_2O$, 0.1% TFA-acetonitrile, to provide the desired product. This procedure provided, with yields ranging from 30% to 70% depending upon the aryl group introduced at the 6-position of the pyrido[3,2-d]pyrimidine ring, the following pure compounds which were characterized by their mass spectrum MS as indicated in table 9.

TABLE 9

| Example | Structure | Name | Observed Mass (M + 1) |
|---|---|---|---|
| 64 | 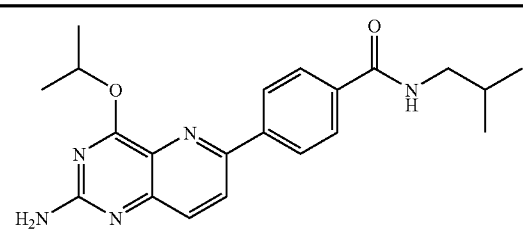 | 4-(2-Amino-4-isopropoxy-pyrido[3,2-d]pyrimidin-6-yl)-N-isobutyl-benzamide | 380.3 |
| 65 | 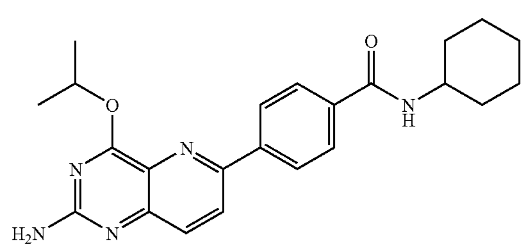 | 4-(2-Amino-4-isopropoxy-pyrido[3,2-d]pyrimidin-6-yl)-N-cyclohexyl-benzamide | 406.5 |
| 66 | 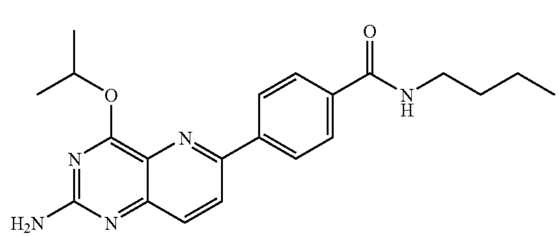 | 4-(2-Amino-4-isopropoxy-pyrido[3,2-d]pyrimidin-6-yl)-N-n-butyl-benzamide | 380.3 |

TABLE 9-continued

| Example | Structure | Name | Observed Mass (M + 1) |
|---|---|---|---|
| 67 | 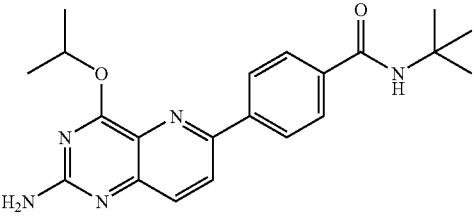 | 4-(2-Amino-4-isopropoxy-pyrido[3,2-d]pyrimidin-6-yl)-N-tert-butyl-benzamide | 380.3 |
| 68 | 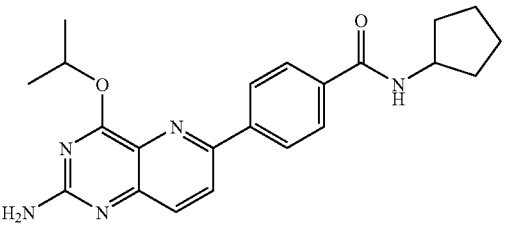 | 4-(2-Amino-4-isopropoxy-pyrido[3,2-d]pyrimidin-6-yl)-N-cyclopentyl-benzamide | 392.3 |
| 69 | 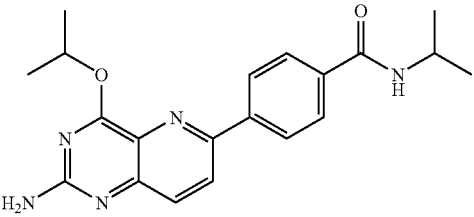 | 4-(2-Amino-4-isopropoxy-pyrido[3,2-d]pyrimidin-6-yl)-N-isopropyl-benzamide | 366.3 |
| 70 | 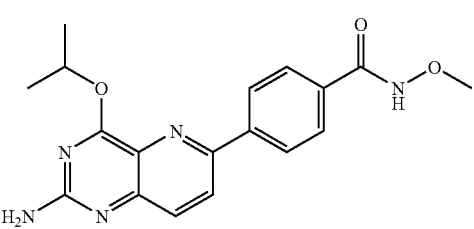 | 4-[2-Amino-4-isopropoxy-pyrido[3,2-d]pyrimidin-6-yl]-N-methoxy-benzamide | 354.3 |
| 71 | 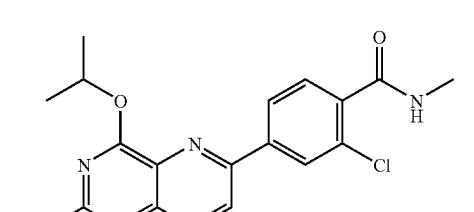 | 4-(2-Amino-4-isopropoxy-pyrido[3,2-d]pyrimidin-6-yl)-2-chloro-N-methyl-benzamide | 372.3 |

TABLE 9-continued

| Example | Structure | Name | Observed Mass (M + 1) |
|---|---|---|---|
| 72 | 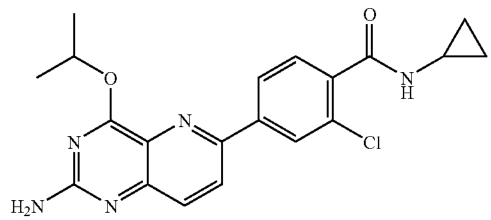 | 4-(2-Amino-4-isopropoxy-pyrido[3,2-d]pyrimidin-6-yl)-2-chloro-N-cyclopropyl-benzamide | 398.1 |
| 73 | 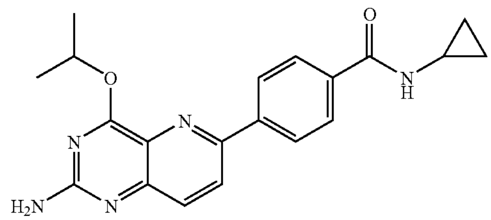 | 4-(2-Amino-4-isopropoxy-pyrido[3,2-d]pyrimidin-6-yl)-N-cyclopropyl-benzamide | 364.3 |
| 74 | 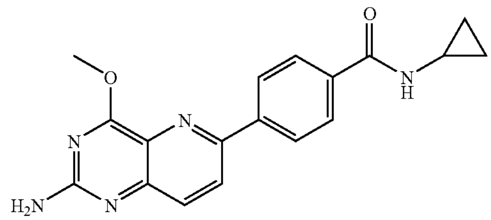 | 4-(2-Amino-4-methoxy-pyrido[3,2-d]pyrimidin-6-yl)-N-cyclopropyl-benzamide | 336.3 |

EXAMPLES 75 AND 76

Synthesis of 6-benzamido-4-(2-methoxy-ethoxy)-pyrido[3,2-d]pyrimidin-2-ylamines

Two different 6-benzamido-4-(2-methoxy-ethoxy)-pyrido[3,2-d]pyrimidin-2-yl-amines were synthesized according to the general procedure outlined in Scheme 15.

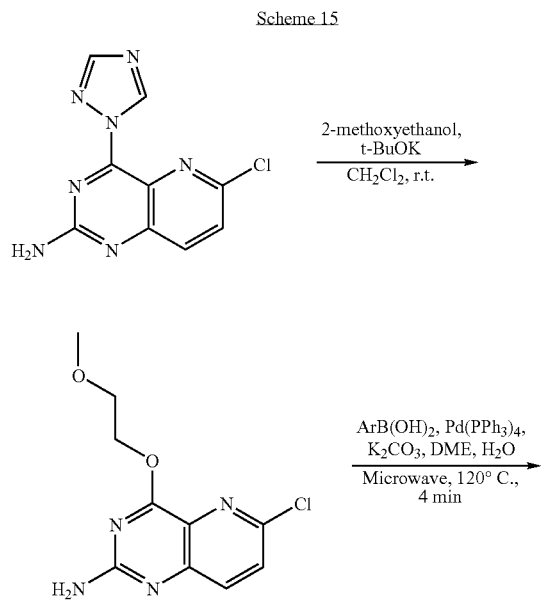

Potassium tert-butoxide (4 mL; 1M in THF) was added to a suspension of 6-Chloro-4-[1,2,4]triazol-1-yl-pyrido[3,2-d]pyrimidin-2-ylamine (1 g) and 2-methoxyethanol (0.32 mL) in DCM (50 mL). After stirring at room temperature for 10 minutes, the mixture was diluted with DCM (100 mL) and washed with brine. The organic layer was dried over $Na_2SO_4$ and concentrated to afford 6-chloro-4-(2-methoxy-ethoxy)-pyrido[3,2-d]pyrimidin-2-ylamine as a beige solid (0.91 g, yield: 90%) which was characterized by its mass spectrum as follows: MS (m/z) 225.0 $[M+H]^+$.

Then a mixture of 6-chloro-4-(2-methoxy-ethoxy)-pyrido[3,2-d]pyrimidin-2-ylamine (15 mg), potassium carbonate (16 mg), tetrakis(triphenylphosphine) palladium (10 mg) and the corresponding boronic acid or pinacol ester (0.08 mmole) in DME (1 mL) and water (0.5 mL) was heated at 100° C. for 10 minutes by microwave. Solvents were concentrated in vacuo and the residue was purified by RP HPLC, using a C18 column with a gradient of $H_2O$, 0.1% TFA-acetonitrile, to provide the desired product. This procedure provided, with yields ranging from 30% to 70% depending upon the aryl group introduced at the 6-position of the pyrido[3,2-d]pyrimidine ring, the following pure compounds which were characterized by their mass spectrum MS as indicated in the following table 10.

TABLE 10

| Example | Structure | Name | Observed Mass (M + 1) |
|---|---|---|---|
| 75 | 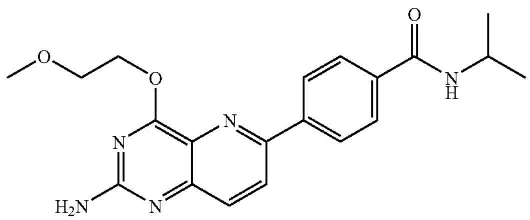 | 4-[2-Amino-4-(2-methoxy-ethoxy)-pyrido[3,2-d]pyrimidin-6-yl]-N-isopropyl-benzamide | 382.1 |
| 76 | 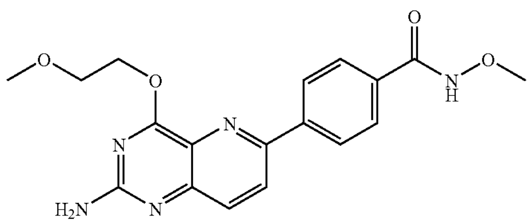 | 4-[2-Amino-4-(2-methoxy-ethoxy)-pyrido[3,2-d]pyrimidin-6-yl]-N-methoxy-benzamide | 370.3 |

EXAMPLES 77 TO 84

Synthesis of 6-benzamido-4-(tetrahydro-furan-3-yloxy)-pyrido[3,2-d]pyrimidin-2-ylamines Various 6-benzamido-4-(tetrahydrofuran-3-yloxy)-pyrido[3,2-d]pyrimidin-2-yl-amines were synthesized according to the synthetic sequence outlined in Scheme 16.

Scheme 16

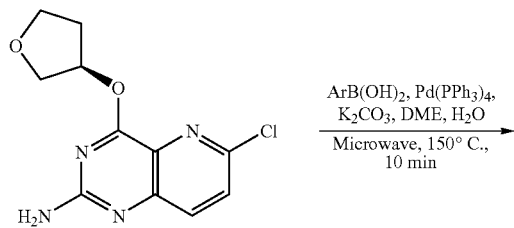

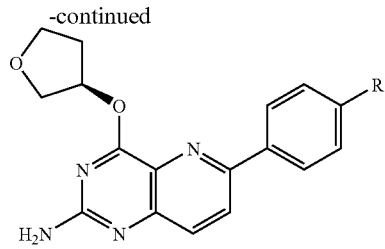

A mixture of N-[6-chloro-4-(tetrahydro-furan-3-yloxy)-pyrido[3,2-d]pyrimidin-2-yl]-acetamide (15 mg), potassium carbonate (16 mg), tetrakis(triphenylphosphine) palladium (10 mg) and a suitable aryl-boronic acid, or a pinacol ester thereof, (0.08 mmole) in DME (1 mL) and water (0.5 mL) was heated to 150° C. for 10 minutes by microwave. Solvents were concentrated in vacuo and the residue was purified by RP HPLC, using a C18 column with a gradient of $H_2O$, 0.1% TFA-acetonitrile, to provide the desired product. This procedure provided, with yields ranging from 10% to 60% depending upon the aryl group introduced at the 6-position of the pyrido[3,2-d]pyrimidine ring, the following pure compounds which were characterized by their mass spectrum MS as indicated in the following table 11.

TABLE 11

| Example | Structure | Name | Observed Mass M + 1 |
|---|---|---|---|
| 77 | 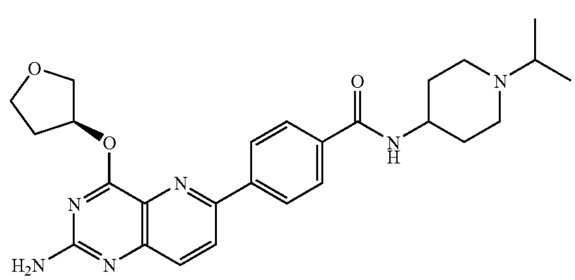 | 4-[2-Amino-4-(tetrahydro-furan-3-yloxy)-pyrido[3,2-d]pyrimidin-6-yl]-N-(1-isopropyl-piperidin-4-yl)-benzamide | 477.3 |

TABLE 11-continued

| Example | Structure | Name | Observed Mass M + 1 |
|---|---|---|---|
| 78 | 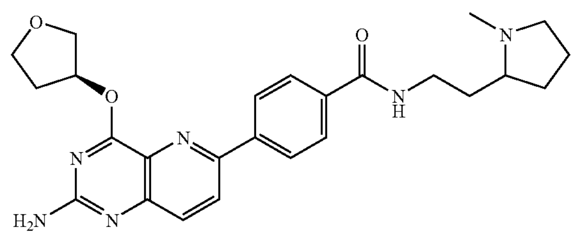 | 4-[2-Amino-4-(tetrahydro-furan-3-yloxy)-pyrido[3,2-d]pyrimidin-6-yl]-N-[2-(1-methyl-pyrrolidin-2-yl)-ethyl]-benzamide | 463.5 |
| 79 | 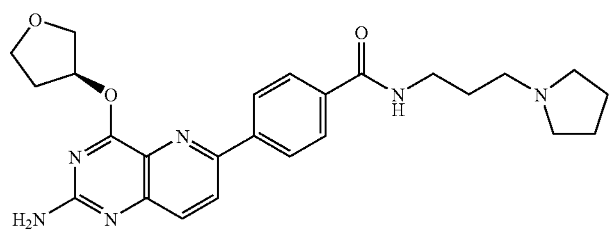 | 4-[2-Amino-4-(tetrahydro-furan-3-yloxy)-pyrido[3,2-d]pyrimidin-6-yl]-N-(3-pyrrolidin-1-yl-propyl)-benzamide | 463.5 |
| 80 | 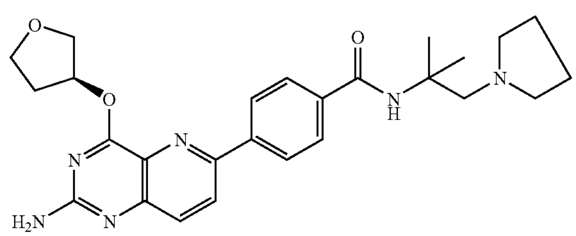 | 4-[2-Amino-4-(tetrahydro-furan-3-yloxy)-pyrido[3,2-d]pyrimidin-6-yl]-N-(1,1-dimethyl-2-pyrrolidin-1-yl-ethyl)-benzamide | 477.3 |
| 81 | 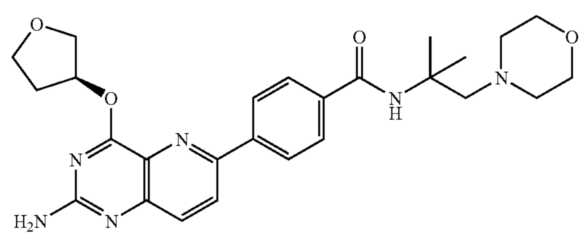 | 4-[2-Amino-4-(tetrahydro-furan-3-yloxy)-pyrido[3,2-d]pyrimidin-6-yl]-N-(1,1-dimethyl-2-morpholin-4-yl-ethyl)-benzamide | 493.3 |
| 82 | 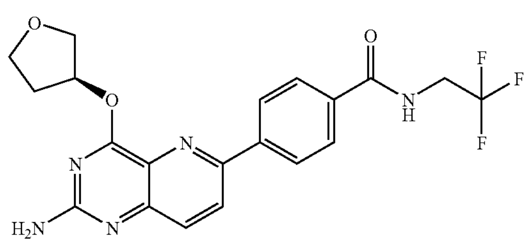 | 4-[2-Amino-4-(tetrahydro-furan-3-yloxy)-pyrido[3,2-d]pyrimidin-6-yl]-N-(2,2,2-trifluoro-ethyl)-benzamide | 434.3 |
| 83 | 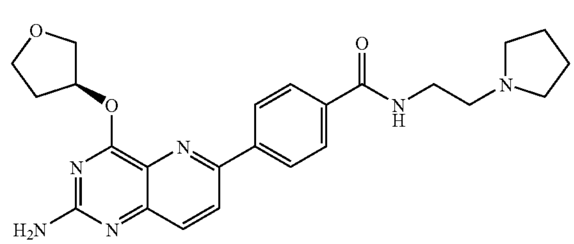 | 4-[2-Amino-4-(tetrahydro-furan-3-yloxy)-pyrido[3,2-d]pyrimidin-6-yl]-N-(2-pyrrolidin-1-yl-ethyl)-benzamide | 449.3 |

TABLE 11-continued

| Example | Structure | Name | Observed Mass M + 1 |
|---|---|---|---|
| 84 | 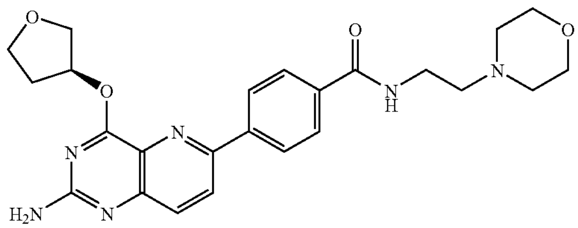 | 4-[2-Amino-4-(tetrahydro-furan-3-yloxy)-pyrido[3,2-d]pyrimidin-6-yl]-N-(2-morpholin-4-yl-ethyl)-benzamide | 465.3 |

EXAMPLES 85 TO 87

Synthesis of 6-benzamido-4-ethoxy-pyrido[3,2-d]pyrimidin-2-yl-amines

Various 6-benzamido-4-ethoxy-pyrido[3,2-d]pyrimidin-2-ylamines were synthesized according to general synthetic sequence outlined in Scheme 17.

Scheme 17

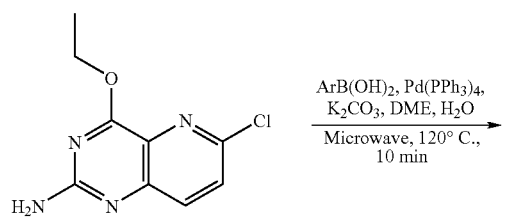

A mixture of 6-chloro-4-ethoxy-pyrido[3,2-d]pyrimidin-2-ylamine (15 mg), potassium carbonate (16 mg), tetrakis(triphenylphosphine) palladium (10 mg) and a suitable arylboronic acid, or a pinacol ester thereof, (0.08 mmol) in DME (1.5 mL) and water (0.5 mL) was heated to 120° C. for 10 minutes by microwave. Solvents were concentrated in vacuuo and the residue was purified by RP HPLC, using a C18 column with a gradient of $H_2O$, 0.1% TFA-acetonitrile, to provide the desired product. This procedure provided, with yields ranging from 10% to 60% depending upon the aryl group introduced at the 6-position of the pyrido[3,2-d]pyrimidine ring, the following pure compounds which were characterized by their mass spectrum MS as indicated in the following table 12.

TABLE 12

| Example | Structure | Name | Observed Mass M + 1 |
|---|---|---|---|
| 85 | 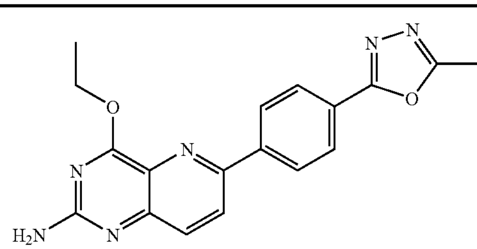 | 4-Ethoxy-6-[4-(5-methyl-[1,3,4]oxadiazol-2-yl)-phenyl]-pyrido[3,2-d]pyrimidin-2-ylamine | 349.3 |
| 86 | 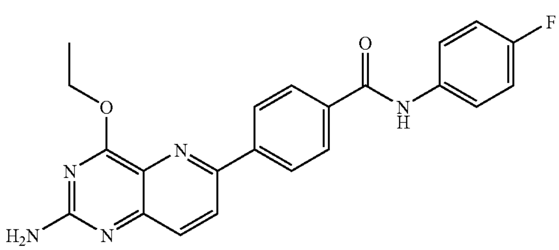 | 4-(2-Amino-4-ethoxy-pyrido[3,2-d]pyrimidin-6-yl)-N-(4-fluoro-phenyl)-benzamide | 404.5 |

TABLE 12-continued

| Example | Structure | Name | Observed Mass M + 1 |
|---|---|---|---|
| 87 | 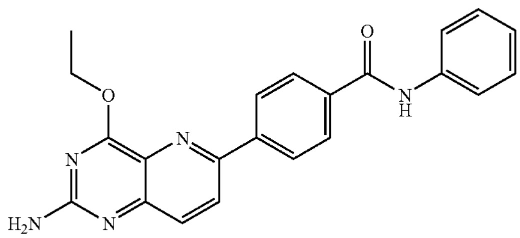 | 4-(2-Amino-4-ethoxy-pyrido[3,2-d]pyrimidin-6-yl)-N-phenyl-benzamide | 386.5 |

EXAMPLE 88

Synthesis of 4-ethoxy-6-(5-methyl-4H-[1,2,4]triazol-3-yl)-pyrido[3,2-d]pyrimidin-2-ylamine The synthesis proceeds in four steps (a) to (d) as shown in the following schemes.

Step a

| Compound | MW | Amount | Moles | Equivalents |
|---|---|---|---|---|
| A | 215.05 | 1 g | 0.00465 | 1 |
| pyridine | | 18 mL | | |
| thioacetamide | 75.13 | 0.383 g | 0.0051 | 1.1 |

Compound A was dissolved in pyridine in a 30 ml microwave reaction vessel. The thioacetamide was added to the solution and the reaction vessel was sealed and heated in a microwave reactor at 200° C. for 10 minutes. The reaction mixture was cooled to room temperature and then partitioned between EtOAc and H₂O. The aqueous layer was extracted 2× with EtOAc. The combined organic layers were washed once with H₂O and twice with a saturated aqueous NaCl solution. The resulting organic fractions were dried over MgSO₄, filtered and concentrated. The residue was purified by flash chromatography on 40 g SiO₂ eluting with 25%-100% EtOAc/Hexane. The fractions corresponding to the more polar product were combined and concentrated to give 200 mg of the desired compound.

Step b

| Compound | MW | Amount | Moles | Equivalents |
|---|---|---|---|---|
| B | 238.08 | 190 mg | 0.000798 | 1 |
| 1,4-dioxane | | 8 ml | | |

| Compound | MW | Amount | Moles | Equivalents |
|---|---|---|---|---|
| H₂O | | 2 ml | | |
| K₂CO₃ | 138.21 | 121 mg | 0.000878 | 1.1 |
| t-Butyl carbonate | 218.25 | 201 ul | 0.000878 | 1.1 |

Compound B was dissolved in 1,4-dioxane/H₂O mixture The K₂CO₃ was then added, followed by t-Butyl carbonate. The reaction mixture was stirred at room temperature for 18 hours. The mixture was partitioned between EtOAc and H₂O. The aqueous layer was extracted two times with EtOAc. The combined organic layers were washed once with H₂O and twice with a saturated aqueous NaCl solution. The organic fractions were dried over MgSO₄, filtered and concentrated. The residue was dried under high vacuum to give 262 mg of desired Boc-protected product.

Step c

| Compound | MW | Amount | Moles | Equivalents |
|---|---|---|---|---|
| C | 338.08 | 100 mg | 0.000296 | 1 |
| THF | | 3 ml | | |
| nBuLi/Hexane | 2.5M | 0.130 ml | 0.000325 | 1.1 |
| B(OMe)₃ | 138.21 | 121 mg | 0.000888 | 3 |

Compound C was dissolved in dry THF under N₂. The solution was cooled to −78° C. in a dry ice/acetone bath and the nBuLi/hexane solution was added over 10 minutes. The reaction was stirred at −78° C. for 15 minutes, whereupon trimethyl borate was added neat. The cold bath was removed and the reaction was allowed to warm to room temperature. After stirring for 2 hours, the reaction was neutralized to pH 7 with 0.5N aqueous HCl. The reaction mixture was partitioned between EtOAc and H₂O. The organic layer was washed with a saturated aqueous NaCl solution and then dried over MgSO$_4$, filtered and concentrated. The crude resulting mixture was used directly for the next Suzuki cross-coupling step.

Step d

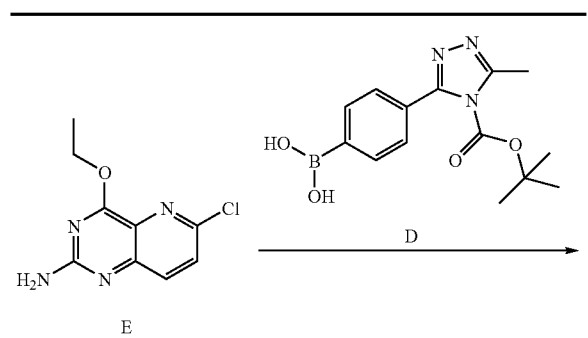

| Compound | MW | Amount | Moles | Equivalents |
|---|---|---|---|---|
| E | 224.65 | 58 mg | 0.0026 | 1 |
| D | | | 0.000296 | 1.14 |
| Dimethoxyethane | | 3.5 ml | 0.000325 | 1.1 |
| 0.4M aq. K$_2$CO$_3$ | 0.4M | 1.3 ml | 0.000520 | 2 |
| Pd(PPh$_3$)$_4$ | 1155 | 10 mg | 0.0000086 | 0.033 |

Compound E was suspended in 2 ml dimethoxyethane. The boronic acid ("D") from previous reaction was dissolved in 1.5 ml dimethoxyethane and added to the suspension of compound E. To the resulting mixture was added the 0.4M aqueous K$_2$CO$_3$ solution followed by Pd(PPh$_3$)$_4$. The reaction vial was sealed and heated at 85° C. for 5 minutes and then at 120° C. for 5 minutes. The reaction mixture was then transferred to a 25 ml round bottom flask and 5 ml of DMF was added. The reaction mixture was heated at 120° C. in an oil bath for 18 hours, then cooled to room temperature and concentrated in vacuo. The residue was partitioned between EtOAc and H$_2$O. The aqueous layer was extracted two times with EtOAc. The combined organic layers were washed once with H$_2$O and two times with a saturated aqueous NaCl solution. The organic fractions were dried over MgSO$_4$, filtered and concentrated. The residue was dissolved in 1.5 ml DMF and this solution was filtered through a 0.45 µm PTFE filter. The filtrate was purified by reverse phase HPLC on C-18 using a gradient of 0.1% H$_2$O and 0.1% acetonitrile. The fraction containing the target compound was identified by reverse phase HPLC/MS. This fraction was concentrated in vacuo to give the desired compound in 6% yield, which was characterized by its mass spectrum as follows: M+H 348.13.

EXAMPLE 89

Synthesis of 2-amino-4-ethoxy-6-(2-(N-(cyclopropyl)carbamoyl)-5-thiophenyl)pyrido[3,2-d]pyrimidine Step (a)-Synthesis of 5-(4,4,5,5-tetramethyl-1,3,2-dioxaborolan-2-yl)-2-thiophene-carboxylic acid

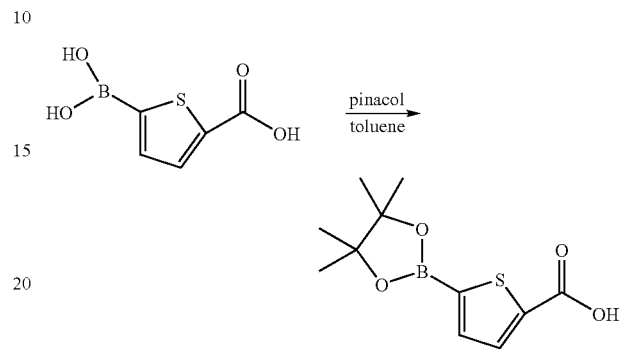

To a solution of 5-(dihydroxyboryl)-2-thiophenecarboxylic acid (4.0 g) in toluene (50 ml) was added pinacol (2.75 g). The reaction mixture was heated at 110-120° C. and the water set free during the reaction was continuously removed by a Dean-Stark apparatus. After 4 hours heating, the reaction mixture was cooled down to room temperature thus providing 5-(4,4,5,5-tetramethyl-1,3,2-dioxaborolan-2-yl)-2-thiophene-carboxylic acid as a white solid which was filtered off (4.43 g, yield: 75%) and used as such for further reaction. The pure compound was characterized by its $^1$H NMR spectrum (300 MHz, CD$_3$OD) as follows: peaks at 1.42 (12H, s), 7.63 (1H, d) and 7.89 (1H, d) ppm.

Step (b)-Synthesis of N-(cyclopropyl)-5-(4,4,5,5-tetramethyl-1,3,2-dioxaborolan-2-yl)-2-thiophenecarboxamide

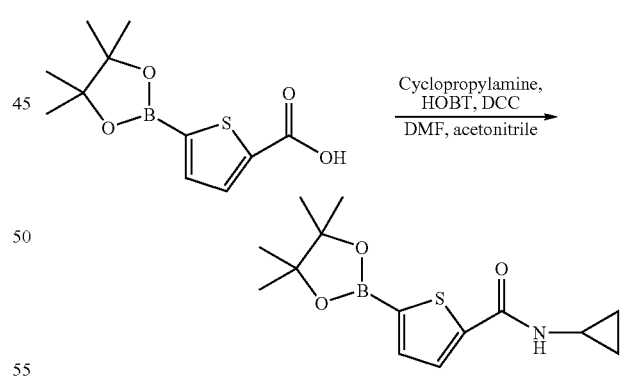

To a solution of 5-(4,4,5,5-tetramethyl-1,3,2-dioxaborolan-2-yl)-2-thiophene-carboxylic acid (200 mg) and 1-hydroxybenzotriazole (117 mg, 0.86 mmole) in acetonitrile (5 ml) and N,N-dimethylformamide (0.5 ml) were added dicyclohexyl-carbodiimide (179 mg). The reaction mixture was stirred at room temperature for 2 hours after which cyclopropylamine (0.11 ml, 1.6 mmole) was added at 0° C. The reaction mixture was stirred at room temperature for an additional 20 hours. The solids formed were filtered off and the filtrate was concentrated under reduced pressure yielding crude N-(cyclopropyl)-5-(4,4,5,5-tetramethyl-1,3,2-dioxaborolan-2-yl)-2-thiophenecarboxamide.

The crude compound was purified by silica gel flash chromatography, the mobile phase being a 5:95 MeOH/CH$_2$Cl$_2$ mixture, resulting in the pure title compound as a white powder (201 mg, yield: 87%) which was characterized by its $^1$H NMR spectrum (300 MHz, CD$_3$OD) as follows: peaks at 0.61 (2H, multiplet), 0.86 (2H, multiplet), 1.34 (12H, s), 2.85 (1H, multiplet), 6.15 (1H, s), 7.52 (1H, d) and 7.55 (1H, d) ppm.

Step (c)-Synthesis of 2-amino-4-ethoxy-6-(2-(N-(cyclopropyl)carbamoyl)-5-thiophenyl)-pyrido[3,2-d]pyrimidine

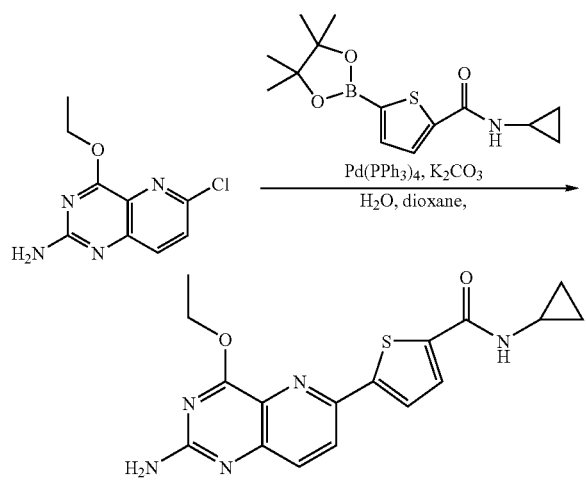

To a solution of 2-amino-4-ethoxy-6-chloropyrido[3,2-d]pyrimidine (50 mg) in 1,4-dioxane (7 ml) and water (2.5 ml) was added N-(cyclopropyl)-5-(4,4,5,5-tetramethyl-1,3,2-dioxaborolan-2-yl)-2-thiophenecarboxamide (72 mg), K$_2$CO$_3$ (77 mg) and tetrakis(triphenylphosphine)palladium(0) (13 mg). The reaction mixture was heated to 90° C. for 1 hour. The reaction mixture was extracted with dichloromethane after which the organic layer was concentrated under reduced pressure. The crude product was purified by silica gel flash chromatography, the mobile phase being a 3:97 MeOH/CH$_2$Cl$_2$ mixture, resulting in the pure title compound as a white powder (64 mg, yield: 81%) which was characterized by its mass spectrum as follows: MS (m/z): 356 ([M+H]$^+$, 100).

EXAMPLE 90

Anti-HCV Assay/Replicon Assay

The anti-HCV activity of the pyrido[3,2-d]pyrimidine derivatives of this invention was tested in a human hepatoma Huh-7 cell line harbouring a HCV replicon. The assay comprised the following steps:

Step 1: Compound Preparation and Serial Dilution
1. for water soluble pyrido[3,2-d]pyrimidine derivatives, a volume of 500 µL of solution in cell media (DMEM, 10% FBS, P/S, L-Glutamine) was prepared with a concentration being twice the concentration of the starting final serial dilution concentration. A volume of 150 µL of the solution was added to the pre-specified wells in column 1 of a 96-well cell culture plate (PerkinElmer, white plate, cat. #6005181, for EC50 assay; black plate, cat. #6005182 for CC50 assay). The rest of the plate, columns 2-12, was filled with 100 µL of cell media. The plate was then placed on a Precision 2000 Workstation to start the serial dilution. Compounds were diluted three times each step from column 1 to column 10. Column 11 was used as a blank control (no compound added).
2. for pyrido[3,2-d]pyrimidine derivatives requiring DMSO to dissolve, serial dilution is performed in 50% DMSO in a 384-well plate. A solution containing a compound at 100-fold concentration of the starting final serial dilution concentration was prepared in 50% DMSO and added to the pre-specified wells in column 1 of a polypropylene 384-well plate. The plate was then placed on a Precision 2000 Workstation to start the serial dilution. After the serial dilution, a volume of 2 µL of the solution was transferred from the 384-well plate to a 96-well cell culture plate containing 100 µL of cell media on a Biomek FX Workstation. The DMSO concentration in the final assay condition was 0.5% after cells are added to the plate and the total volume in each well is brought to 200 µL.

Step 2: to each well of the serial dilution plate prepared above, 100 µL of cell media containing 6000 suspended Huh-7 HCV replicon cells was added with a Multidrop workstation. The plates were incubated for 3 days at 37° C. with 5% CO$_2$.

Step 3: Detection:
a) for the EC$_{50}$ assay, the media in a 96-well cell culture plate was aspirated with a Biotek EL405 plate-washer. A volume of 200 µL of a solution containing a 1:1 mixture of cell-lysis buffer (Promega, Luciferase Cell Culture Lysis 5X Reagent, cat. #E1531) and luciferase substrate solution (Promega, Luciferase Assay, cat. # E4550) was added to each well of the plate with Multidrop. The plate was incubated for 30 minutes at room temperature before the luminescence signal was measured with a TopCount plate-reader.
b) for the CC$_{50}$ assay, a volume of 100 µL of pre-mixed CellTiter-Glo (Promega, cat. # G7572) solution is added directly to the cell culture in each well of the plate and the luminescence signal is measured with a TopCount plate-reader after 10 minutes of incubation at room temperature.

Table 13 below shows EC$_{50}$ and CC$_{50}$ ranges of derivatives tested in this assay. Results in table 13 are expressed by the following data:
the 50% effective concentration (EC$_{50}$), i.e. the concentration that protects 50% of the cell monolayer from virus-induced cythopathic effect, and
the 50% cytostatic concentration (CC$_{50}$), i.e. the concentration that results in 50% inhibition of cell growth.

TABLE 13

| Example | EC$_{50}$ (A < 300 nM; B 300-1,000 nM; C > 1,000 nM) | CC$_{50}$ (A < 10 µM; B 10-20 µM; C > 20 µM) |
|---|---|---|
| 1 | A | A |
| 2 | B | C |
| 3 | B | C |
| 4 | C | C |
| 5 | A | C |
| 6 | B | B |
| 7 | B | C |
| 8 | A | C |
| 9 | A | B |
| 10 | B | C |
| 11 | A | C |
| 12 | A | A |
| 13 | A | C |
| 14 | A | C |
| 15 | A | C |
| 16 | A | B |
| 17 | A | A |

TABLE 13-continued

| Example | EC$_{50}$ (A < 300 nM; B 300-1,000 nM; C > 1,000 nM) | CC$_{50}$ (A < 10 µM; B 10-20 µM; C > 20 µM) |
|---|---|---|
| 18 | B | C |
| 19 | B | C |
| 20 | A | C |
| 21 | B | C |
| 22 | A | C |
| 23 | A | C |
| 24 | C | C |
| 25 | A | B |
| 26 | A | C |
| 27 | A | C |
| 28 | A | C |
| 29 | A | C |
| 30 | A | C |
| 31 | B | B |
| 32 | B | C |
| 33 | A | C |
| 34 | A | C |
| 35 | B | C |
| 36 | A | C |
| 37 | A | C |
| 38 | A | C |
| 39 | A | C |
| 40 | B | C |
| 41 | A | C |
| 42 | A | C |
| 43 | C | C |
| 44 | B | C |
| 45 | A | C |
| 46 | A | C |
| 47 | A | B |
| 48 | A | C |
| 49 | B | C |
| 50 | B | C |
| 51 | A | C |
| 52 | A | A |
| 53 | A | C |
| 54 | A | C |
| 55 | C | C |
| 56 | B | C |
| 57 | B | C |
| 58 | C | C |
| 59 | B | C |
| 60 | C | C |
| 61 | B | C |
| 62 | C | C |
| 63 | A | B |
| 64 | B | C |
| 65 | C | C |
| 66 | B | C |
| 67 | B | C |
| 68 | B | C |
| 69 | A | C |
| 70 | A | C |
| 71 | C | C |
| 72 | C | C |
| 73 | A | C |
| 74 | B | B |
| 75 | B | C |
| 76 | B | C |
| 77 | C | C |
| 78 | C | C |
| 79 | B | C |
| 80 | A | B |
| 81 | A | C |
| 82 | A | B |
| 83 | A | C |
| 84 | A | C |
| 85 | C | C |
| 86 | B | C |
| 87 | C | C |
| 88 | B | B |
| 89 | A | C |

EXAMPLES 91 TO 94

Synthesis of 6-benzamido-N4-(2-ethoxyethyl)-pyrido[3,2-d]pyrimidin-2-ylamines

The following 6-benzamido-N4-(2-ethoxyethyl)-pyrido[3,2-d]pyrimidin-2-ylamines are synthesized according to the synthetic route of Scheme 2, except for the use of 2-ethoxyethylamine instead of 2-methoxyethylamine as a starting reactant, and are obtained in similar yields as the compounds of examples 8-11:

→N-{4-[2-amino-4-(2-ethoxy-ethylamino)-pyrido[3,2-d]pyrimidin-6-yl]-phenyl}-propionamide (example 91), N-{4-[2-amino-4-(2-ethoxy-ethylamino)-pyrido[3,2-d]pyrimidin-6-yl]-phenyl}-isobutyramide (example 92), {4-[2-amino-4-(2-ethoxy-ethylamino)-pyrido[3,2-d]pyrimidin-6-yl]-phenyl}-carbamic acid methyl ester (example 93), and 4-[2-amino-4-(2-ethoxy-ethylamino)-pyrido[3,2-d]pyrimidin-6-yl]-N-cyclopropyl-benzamide (example 94).

EXAMPLES 95 TO 98

Synthesis of 6-benzamido-N4-(2-isopropoxyethyl)-pyrido[3,2-d]pyrimidin-2-ylamines The following 6-benzamido-N4-(2-isopropoxy-ethyl)-pyrido[3,2-d]pyrimidin-2-ylamines are synthesized according to the synthetic route of Scheme 2, except for the use of 2-isopropoxyethylamine instead of 2-methoxyethylamine as a starting reactant, and are obtained in similar yields as the compounds of examples 8-11:

N-{4-[2-amino-4-(2-isopropoxy-ethylamino)-pyrido[3,2-d]pyrimidin-6-yl]-phenyl}-propionamide (example 95), N-{4-[2-amino-4-(2-isopropoxy-ethylamino)-pyrido[3,2-d]pyrimidin-6-yl]-phenyl}-isobutyramide (example 96), {4-[2-amino-4-(2-isopropoxy-ethylamino)-pyrido[3,2-d]pyrimidin-6-yl]-phenyl}-carbamic acid methyl ester (example 97), and 4-[2-amino-4-(2-isopropoxy-ethylamino)-pyrido[3,2-d]pyrimidin-6-yl]-N-cyclopropyl-benzamide (example 98).

EXAMPLES 99 TO 102

Synthesis of 6-benzamido-N4-(2-n-propoxyethyl)-pyrido[3,2-d]pyrimidin-2-ylamines The following 6-benzamido-N4-(2-isopropoxyethyl)-pyrido[3,2-d]pyrimi-din-2-ylamines are synthesized according to the synthetic route of Scheme 2, except for the use of 2-n-propoxyethylamine instead of 2-methoxyethylamine as a starting reactant, and are obtained in similar yields as the compounds of examples 8-11:

N-{4-[2-amino-4-(2-n-propoxy-ethylamino)-pyrido[3,2-d]pyrimidin-6-yl]-phenyl}-propionamide (example 99), N-{4-[2-amino-4-(2-n-propoxy-ethylamino)-pyrido[3,2-d]pyrimidin-6-yl]-phenyl}-isobutyramide (example 100), {4-[2-amino-4-(2-n-propoxy-ethylamino)-pyrido[3,2-d]pyrimidin-6-yl]-phenyl}-carbamic acid methyl ester (example 101), and 4-[2-amino-4-(2-n-propoxy-ethylamino)-pyrido[3,2-d]pyrimidin-6-yl]-N-cyclopropyl-benzamide (example 102).

EXAMPLES 103 TO 106

Synthesis of 6-benzamido-N4-(2-tert-butoxyethyl)-pyrido[3,2-d]pyrimidin-2-ylamines The following 6-benzamido-N4-(2-tert-butoxyethyl)-pyrido[3,2-d]pyrimidin-2-ylamines are synthesized according to the synthetic route of Scheme 2, except for the use of 2-tert-butoxyethylamine instead of 2-methoxyethylamine as a starting reactant, and are obtained in similar yields as the compounds of examples 8-11:

N-{4-[2-amino-4-(2-tert-butoxyethylamino)-pyrido[3,2-d]pyrimidin-6-yl]-phenyl}-propionamide (example 103),
N-{4-[2-amino-4-(2-tert-butoxyethylamino)-pyrido[3,2-d]pyrimidin-6-yl]-phenyl}-isobutyramide (example 104),
{4-[2-amino-4-(2-tert-butoxyethylamino)-pyrido[3,2-d]pyrimidin-6-yl]-phenyl}-carbamic acid methyl ester (example 105), and
4-[2-amino-4-(2-tert-butoxyethylamino)-pyrido[3,2-d]pyrimidin-6-yl]-N-cyclopropyl-benzamide (example 106).

EXAMPLES 107 TO 110

Synthesis of 6-benzamido-N4-(3-methoxypropyl)-pyrido[3,2-d]pyrimidin-2-ylamines

The following 6-benzamido-N4-(3-methoxypropyl)-pyrido[3,2-d]pyrimi-din-2-ylamines are synthesized according to the synthetic route of Scheme 2, except for the use of 3-methoxypropylamine instead of 2-methoxyethylamine as a starting reactant, and are obtained in similar yields as the compounds of examples 8-11:

N-{4-[2-amino-4-(3-methoxypropylamino)-pyrido[3,2-d]pyrimidin-6-yl]-phenyl}-propionamide (example 107),
N-{4-[2-amino-4-(3-methoxypropylamino)-pyrido[3,2-d]pyrimidin-6-yl]-phenyl}-isobutyramide (example 108),
{4-[2-amino-4-(3-methoxypropylamino)-pyrido[3,2-d]pyrimidin-6-yl]-phenyl}-carbamic acid methyl ester (example 109), and
4-[2-amino-4-(3-methoxypropylamino)-pyrido[3,2-d]pyrimidin-6-yl]-N-cyclopropyl-benzamide (example 110).

EXAMPLES 111 TO 114

Synthesis of 6-benzamido-N4-(3-ethoxypropyl)-pyrido[3,2-d]pyrimidin-2-ylamines

The following 6-benzamido-N4-(3-ethoxypropyl)-pyrido[3,2-d]pyrimi-din-2-ylamines are synthesized according to the synthetic route of Scheme 2, except for the use of 3-ethoxypropylamine instead of 2-methoxyethylamine as a starting reactant, and are obtained in similar yields as the compounds of examples 8-11:

N-{4-[2-amino-4-(3-ethoxypropylamino)-pyrido[3,2-d]pyrimidin-6-yl]-phenyl}-propionamide (example 111),
N-{4-[2-amino-4-(3-ethoxypropylamino)-pyrido[3,2-d]pyrimidin-6-yl]-phenyl}-isobutyramide (example 112),
{4-[2-amino-4-(3-ethoxypropylamino)-pyrido[3,2-d]pyrimidin-6-yl]-phenyl}-carbamic acid methyl ester (example 113), and
4-[2-amino-4-(3-ethoxypropylamino)-pyrido[3,2-d]pyrimidin-6-yl]-N-cyclopropyl-benzamide (example 114).

EXAMPLES 115 TO 118

Synthesis of 6-benzamido-N4-(2-methoxybutyl)-pyrido[3,2-d]pyrimidin-2-ylamines

The following 6-benzamido-N4-(3-methoxypropyl)-pyrido[3,2-d]pyrimi-din-2-ylamines are synthesized according to the synthetic route of Scheme 2, except for the use of 2-methoxybutylamine instead of 2-methoxyethylamine as a starting reactant, and are obtained in similar yields as the compounds of examples 8-11:

N-{4-[2-amino-4-(2-methoxybutylamino)-pyrido[3,2-d]pyrimidin-6-yl]-phenyl}-propionamide (example 115),
N-{4-[2-amino-4-(2-methoxybutylamino)-pyrido[3,2-d]pyrimidin-6-yl]-phenyl}-isobutyramide (example 116),
{4-[2-amino-4-(2-methoxybutylamino)-pyrido[3,2-d]pyrimidin-6-yl]-phenyl}-carbamic acid methyl ester (example 117), and
4-[2-amino-4-(2-methoxybutylamino)-pyrido[3,2-d]pyrimidin-6-yl]-N-cyclopropyl-benzamide (example 118).

EXAMPLES 119 TO 121

Synthesis of 6-benzamido-4-(2-ethoxy-ethoxy)-pyrido[3,2-d]pyrimidin-2-ylamines

The following 6-benzamido-4-(2-ethoxy-ethoxy)-pyrido[3,2-d]pyrimidin-2-ylamines are synthesized according to the synthetic route of Scheme 5, except for the use of 2-ethoxyethanol instead of 2-methoxyethanol as a starting reactant, and are obtained in similar yields as the compounds of examples 18-20:

N-{4-[2-amino-4-(2-ethoxy-ethoxy)-pyrido[3,2-d]pyrimidin-6-yl]-phenyl}-propionamide (example 119),
{4-[2-amino-4-(2-ethoxy-ethoxy)-pyrido[3,2-d]pyrimidin-6-yl]-phenyl}-carbamic acid methyl ester (example 120), and
4-[2-amino-4-(2-ethoxy-ethoxy)-pyrido[3,2-d]pyrimidin-6-yl]-N-cyclopropyl-benzamide (example 121).

EXAMPLES 122 TO 124

Synthesis of 6-benzamido-4-(2-n-propoxy-ethoxy)-pyrido[3,2-d]pyrimidin-2-ylamines The following 6-benzamido-4-(2-n-propoxy-ethoxy)-pyrido[3,2-d]pyrimi-din-2-ylamines are synthesized according to the synthetic route of Scheme 5, except for the use of 2-n-propoxyethanol instead of 2-methoxyethanol as a starting reactant, and are obtained in similar yields as the compounds of examples 18-20:

N-{4-[2-amino-4-(2-n-propoxy-ethoxy)-pyrido[3,2-d]pyrimidin-6-yl]-phenyl}-propionamide (example 122),
{4-[2-amino-4-(2-n-propoxy-ethoxy)-pyrido[3,2-d]pyrimidin-6-yl]-phenyl}-carbamic acid methyl ester (example 123), and
4-[2-amino-4-(2-n-propoxy-ethoxy)-pyrido[3,2-d]pyrimidin-6-yl]-N-cyclopropylbenzamide (example 124).

EXAMPLES 125 TO 127

Synthesis of 6-benzamido-4-(2-n-propoxy-ethoxy)-pyrido[3,2-d]pyrimidin-2-ylamines The following 6-benzamido-4-(2-isopropoxy-ethoxy)-pyrido[3,2-d]pyrimi-din-2-ylamines are synthesized according to the synthetic route of Scheme 5, except for the use of 2-n-propoxyethanol instead of 2-methoxyethanol as a starting reactant, and are obtained in similar yields as the compounds of examples 18-20:

N-{4-[2-amino-4-(2-isopropoxy-ethoxy)-pyrido[3,2-d]pyrimidin-6-yl]-phenyl}-propionamide (example 125),
{4-[2-amino-4-(2-isopropoxy-ethoxy)-pyrido[3,2-d]pyrimidin-6-yl]-phenyl}-carbamic acid methyl ester (example 126), and
4-[2-amino-4-(2-isopropoxy-ethoxy)-pyrido[3,2-d]pyrimidin-6-yl]-N-cyclopropylbenzamide (example 127).

EXAMPLES 128 TO 130

Synthesis of 6-benzamido-4-(3-ethoxy-propoxy)-pyrido[3,2-d]pyrimidin-2-ylamines

The following 6-benzamido-4-(3-ethoxy-propoxy)-pyrido[3,2-d]pyrimi-din-2-ylamines are synthesized according to the synthetic route of Scheme 5, except for the use of 3-ethoxy-1-propanol instead of 2-methoxyethanol as a starting reactant, and are obtained in similar yields as the compounds of examples 18-20:
N-{4-[2-amino-4-(3-ethoxy-propoxy)-pyrido[3,2-d]pyrimi-din-6-yl]-phenyl}-propionamide (example 128),
{4-[2-amino-4-(3-ethoxy-propoxy)-pyrido[3,2-d]pyrimidin-6-yl]-phenyl}-carbamic acid methyl ester (example 129), and
4-[2-amino-4-(3-ethoxy-propoxy)-pyrido[3,2-d]pyrimidin-6-yl]-N-cyclopropyl-benzamide (example 130).

EXAMPLES 131 TO 133

Synthesis of 6-benzamido-4-(4-ethoxybut-1-oxy)-pyrido[3,2-d]pyrimidin-2-ylamines The following 6-benzamido-4-(4-ethoxybut-1-oxy)-pyrido[3,2-d]pyrimi-din-2-ylamines are synthesized according to the synthetic route of Scheme 5, except for the use of 4-ethoxy-1-butanol instead of 2-methoxyethanol as a starting reactant, and are obtained in similar yields as the compounds of examples 18-20:
N-{4-[2-amino-4-(4-ethoxybut-1-oxy)-pyrido[3,2-d]pyrimidin-6-yl]-phenyl}-propionamide (example 131),
{4-[2-amino-4-(4-ethoxy-propoxy)-pyrido[3,2-d]pyrimidin-6-yl]-phenyl}-carbamic acid methyl ester (example 132), and
4-[2-amino-4-(4-ethoxybut-1-oxy)-pyrido[3,2-d]pyrimidin-6-yl]-N-cyclopropyl-benzamide (example 133).

EXAMPLES 134 AND 135

Synthesis of N-{4-[2-amino-4-fluoroalkoxy-pyrido[3,2-d]pyrimidin-6-yl]-phenyl}-isobutyramides The following intermediates and final compounds are synthesized according to the synthetic route of Scheme 6, except for the use of 3-fluoropropan-1-ol and 4-fluoro-1-butanol instead of 2-fluoroethanol as a starting reactant, and are obtained in similar yields as the compound of example 21:
6-chloro-4-(3-fluoropropoxy)-pyrido[3,2-d]pyrimidin-2-ylamine,
N-{4-[2-amino-4-(3-fluoropropoxy)-pyrido[3,2-d]pyrimi-din-6-yl]-phenyl}-isobutyramide (example 134),
6-chloro-4-(4-fluorobutoxy)-pyrido[3,2-d]pyrimidin-2-ylamine, and
N-{4-[2-amino-4-(4-fluorobutoxy)-pyrido[3,2-d]pyrimidin-6-yl]-phenyl}-isobutyramide (example 135).

EXAMPLES 136 TO 145

Synthesis of 6-benzamido-4-(tert-butoxy)-pyrido[3,2-d]pyrimidin-2-ylamines

The following 6-benzamido-4-(tert-butoxy)-pyrido[3,2-d]pyrimidin-2-ylamines are synthesized according to the synthetic route of Scheme 14, except for the use of tert-butanol instead of 2-propanol as a starting reactant, and are obtained in similar yields as the compounds of examples 64-73:
4-(2-amino-4-tert-butoxy-pyrido[3,2-d]pyrimidin-6-yl)-N-isobutyl-benzamide (example 136),
4-(2-amino-4-tert-butoxy-pyrido[3,2-d]pyrimidin-6-yl)-N-cyclohexyl-benzamide (example 137),
4-(2-amino-4-tert-butoxy-pyrido[3,2-d]pyrimidin-6-yl)-N-n-butyl-benzamide (example 138),
4-(2-amino-4-tert-butoxy-pyrido[3,2-d]pyrimidin-6-yl)-N-tert-butyl-benzamide (example 139),
4-(2-amino-4-tert-butoxy-pyrido[3,2-d]pyrimidin-6-yl)-N-cyclopentyl-benzamide (example 140),
4-(2-amino-4-tert-butoxy-pyrido[3,2-d]pyrimidin-6-yl)-N-isopropyl-benzamide (example 141),
4-[2-amino-4-tert-butoxy-pyrido[3,2-d]pyrimidin-6-yl]-N-methoxy-benzamide (example 142),
4-(2-amino-4-tert-butoxy-pyrido[3,2-d]pyrimidin-6-yl)-2-chloro-N-methyl-benzamide (example 143),
4-(2-amino-4-tert-butoxy-pyrido[3,2-d]pyrimidin-6-yl)-2-chloro-N-cyclopropyl-benzamide (example 144), and
4-(2-amino-4-tert-butoxy-pyrido[3,2-d]pyrimidin-6-yl)-N-cyclopropyl-benzamide (example 145).

EXAMPLES 146 TO 155

Synthesis of 6-benzamido-4-(tert-pentoxy)-pyrido[3,2-d]pyrimidin-2-ylamines

The following 6-benzamido-4-(tert-pentoxy)-pyrido[3,2-d]pyrimidin-2-ylamines are synthesized according to the synthetic route of Scheme 14, except for the use of tert-pentanol instead of 2-propanol as a starting reactant, and are obtained in similar yields as the compounds of examples 64-73:
4-(2-amino-4-tert-pentoxy-pyrido[3,2-d]pyrimidin-6-yl)-N-isobutyl-benzamide (example 146),
4-(2-amino-4-tert-pentoxy-pyrido[3,2-d]pyrimidin-6-yl)-N-cyclohexyl-benzamide (example 147),
4-(2-amino-4-tert-pentoxy-pyrido[3,2-d]pyrimidin-6-yl)-N-n-butyl-benzamide (example 148),
4-(2-amino-4-tert-pentoxy-pyrido[3,2-d]pyrimidin-6-yl)-N-tert-butyl-benzamide (example 149),
4-(2-amino-4-tert-pentoxy-pyrido[3,2-d]pyrimidin-6-yl)-N-cyclopentyl-benzamide (example 150),
4-(2-amino-4-tert-pentoxy-pyrido[3,2-d]pyrimidin-6-yl)-N-isopropyl-benzamide (example 151),
4-[2-amino-4-tert-pentoxy-pyrido[3,2-d]pyrimidin-6-yl]-N-methoxy-benzamide (example 152),
4-(2-amino-4-tert-pentoxy-pyrido[3,2-d]pyrimidin-6-yl)-2-chloro-N-methyl-benzamide (example 153),
4-(2-amino-4-tert-pentoxy-pyrido[3,2-d]pyrimidin-6-yl)-2-chloro-N-cyclopropyl-benzamide (example 154), and
4-(2-amino-4-tert-pentoxy-pyrido[3,2-d]pyrimidin-6-yl)-N-cyclopropyl-benzamide (example 155).

The invention claimed is:

1. A pyrido(3,2-d)pyrimidine derivative, having the structural formula:

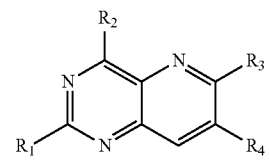

wherein:
$R_1$ is amino,
$R_2$ is selected from the group consisting of N-morpholinyl, N-thiomorpholinyl, N-thiomorpholinyl dioxide, mono- $C_{2-6}$ alkyl amino wherein said $C_{2-6}$ alkyl is optionally substituted with methylsulfonyl or $C_{1-4}$ alkoxy; $C_{1-6}$ alkoxy-$C_{1-6}$ alkoxy wherein said $C_{1-6}$ alkoxy is optionally substituted with a substituent selected from the group consisting of halogen and heterocyclic-oxy;

$R_4$ is hydrogen;

$R_3$ is a mono-substituted phenyl group substituted with —NH-Het$^1$ wherein said Het$^1$ is attached to the adjacent nitrogen atom through a carbon atom;

Het$^1$ is a heterocyclic group;

or a pharmaceutical acceptable addition salt or a stereochemical isomeric form thereof or a N-oxide thereof.

2. A pyrido(3,2-d)pyrimidine derivative having the structural formula:

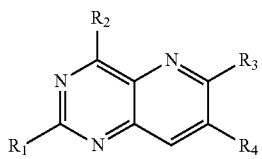

wherein:

$R_1$ is amino, $R_2$ is selected from the group consisting of N-morpholinyl, N-thiomorpholinyl, N-thiomorpholinyl dioxide, mono-$C_{2-6}$ alkyl amino wherein said $C_{2-6}$ alkyl is optionally substituted with methylsulfonyl or $C_{1-4}$ alkoxy; $C_{1-6}$ alkoxy-$C_{1-6}$ alkoxy wherein said $C_{1-6}$ alkoxy is optionally substituted with a substituent selected from the group consisting of halogen and heterocyclic-oxy;

$R_4$ is hydrogen;

$R_3$ is selected from the group consisting of, mono-substituted aryl groups and disubstituted aryl groups, wherein at least one substituent of said aryl group is selected from the group consisting of —CONHR$_5$, —NHCOR$_6$, —NHSO$_2$R$_7$, —NH-Het$^1$ and Het$^2$;

cyclopropylcarbamoylthien-2-yl, —NH-Het$^1$ and a N-containing heterocyclic group selected from thiazolyl and triazolyl, said N-containing heterocyclic group being optionally substituted with oxo or $C_{1-6}$ alkyl or amino;

$R_5$ is selected from the group consisting of $C_{3-10}$ cycloalkyl; $C_{1-6}$ alkyl wherein said $C_{1-6}$ alkyl is optionally substituted with one or more substituents independently selected from the group consisting of amino, alkylamino, dialkylamino, halogen and non-aromatic heterocyclic groups; $C_{1-6}$ alkoxy; heterocyclic groups wherein said heterocyclic group is optionally substituted with $C_{1-6}$ alkyl; and phenyl optionally substituted with halogen;

$R_6$ is selected from the group consisting of $C_{1-6}$ alkyl wherein said $C_{1-6}$ alkyl is optionally substituted with one or more substituents independently selected from the group consisting of amino, halogen and hydroxyl; $C_{1-6}$ alkoxy; heterocyclic groups wherein said heterocyclic group is optionally substituted with one or more substituents selected from the group consisting of $C_{1-6}$ alkyl, acylamino and oxo; $C_{3-10}$ cycloalkyl, wherein said $C_{3-10}$ cycloalkyl is optionally substituted with amino or hydroxyl; and aryl groups, wherein said aryl group is optionally substituted with $C_{1-6}$ alkyl;

$R_7$ is selected from the group consisting of methyl, ethyl, trifluoroethyl and isopropyl;

Het$^1$ is a heterocyclic group;

Het$^2$ is a N-containing heterocyclic group optionally substituted with oxo or $C_{1-6}$ alkyl or amino;

or a pharmaceutical acceptable addition salt or a stereochemical isomeric form thereof or a N-oxide thereof.

* * * * *